(12) United States Patent
Battrell et al.

(10) Patent No.: US 8,431,389 B2
(45) Date of Patent: Apr. 30, 2013

(54) PORTABLE HIGH GAIN FLUORESCENCE DETECTION SYSTEM

(75) Inventors: C. Frederick Battrell, Redmond, WA (US); Troy D. Daiber, Auburn, WA (US)

(73) Assignee: Micronics, Inc., Redmond, WA (US)

( * ) Notice: Subject to any disclaimer, the term of this patent is extended or adjusted under 35 U.S.C. 154(b) by 0 days.

(21) Appl. No.: 13/245,124

(22) Filed: Sep. 26, 2011

(65) Prior Publication Data

US 2012/0115214 A1    May 10, 2012

Related U.S. Application Data

(63) Continuation of application No. 13/191,120, filed on Jul. 26, 2011, now Pat. No. 8,329,453, which is a continuation of application No. PCT/US2010/022581, filed on Jan. 29, 2010.

(60) Provisional application No. 61/148,843, filed on Jan. 30, 2009.

(51) Int. Cl.
*C12M 1/34* (2006.01)

(52) U.S. Cl.
USPC ..................... 435/287.2; 422/82.05

(58) Field of Classification Search ............... 435/287.2; 356/246, 445; 250/459; 73/1.22, 1.41, 1.45, 73/1.56, 61.48, 61.69, 64.43, 800; 359/240, 359/247, 290, 309, 318, 416–418
See application file for complete search history.

(56) References Cited

U.S. PATENT DOCUMENTS

| 4,833,332 | A | 5/1989 | Robertson, Jr. et al. |
| 5,543,026 | A | 8/1996 | Hoff et al. |
| 2007/0009383 | A1* | 1/2007 | Bedingham et al. ............ 422/63 |
| 2008/0260586 | A1* | 10/2008 | Boamfa ..................... 422/82.08 |
| 2008/0297792 | A1* | 12/2008 | Kim et al. .................... 356/317 |

FOREIGN PATENT DOCUMENTS

WO    WO 2008101732 A1 *   8/2008

OTHER PUBLICATIONS

International Search Report for PCT/US2010/022581, mailed Apr. 26, 2010, 4 pages.

* cited by examiner

*Primary Examiner* — Michael Hobbs
(74) *Attorney, Agent, or Firm* — Seed IP Law Group PLLC

(57) ABSTRACT

An instrument for fluorometric assays in liquid samples is disclosed. The instrument may include multiple optical channels for monitoring a first fluorophore associated with a target analyte and a second fluorophore associated with a control. The disclosed instrument finds utility in any number of applications, including microfluidic molecular biological assays based on PCR amplification of target nucleic acids and fluorometric assays in general.

18 Claims, 23 Drawing Sheets

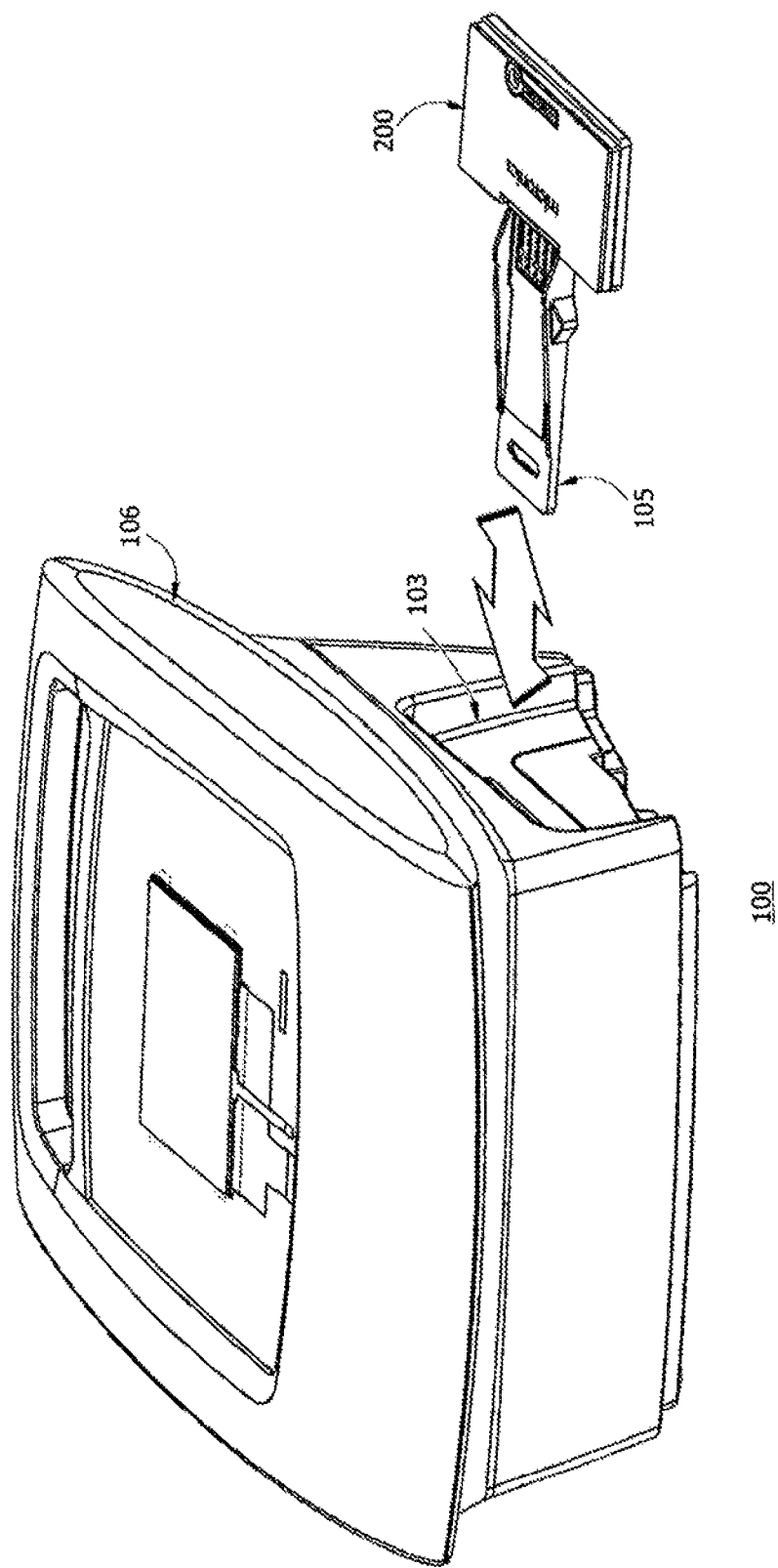

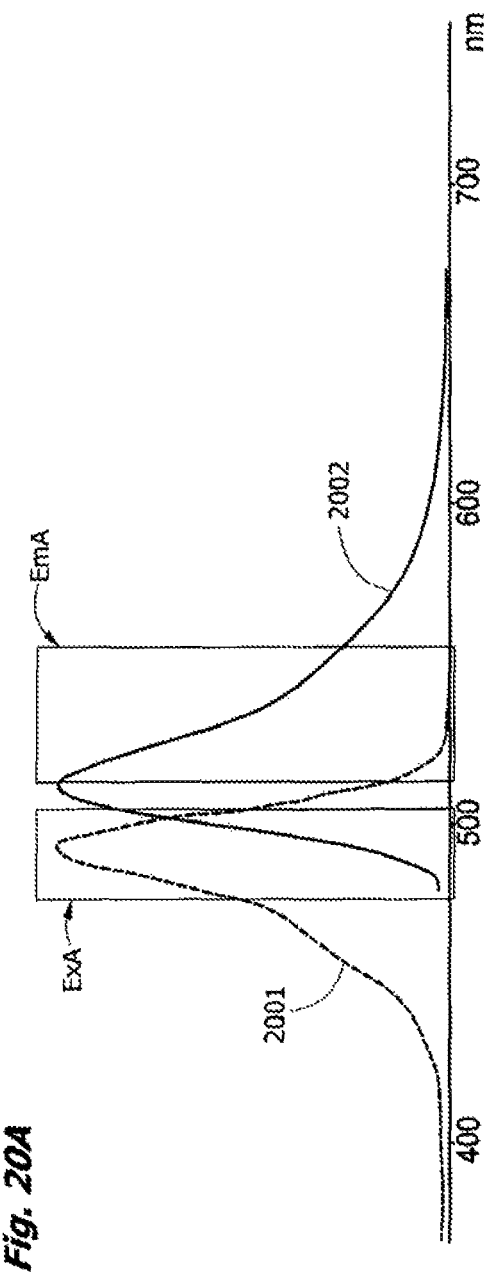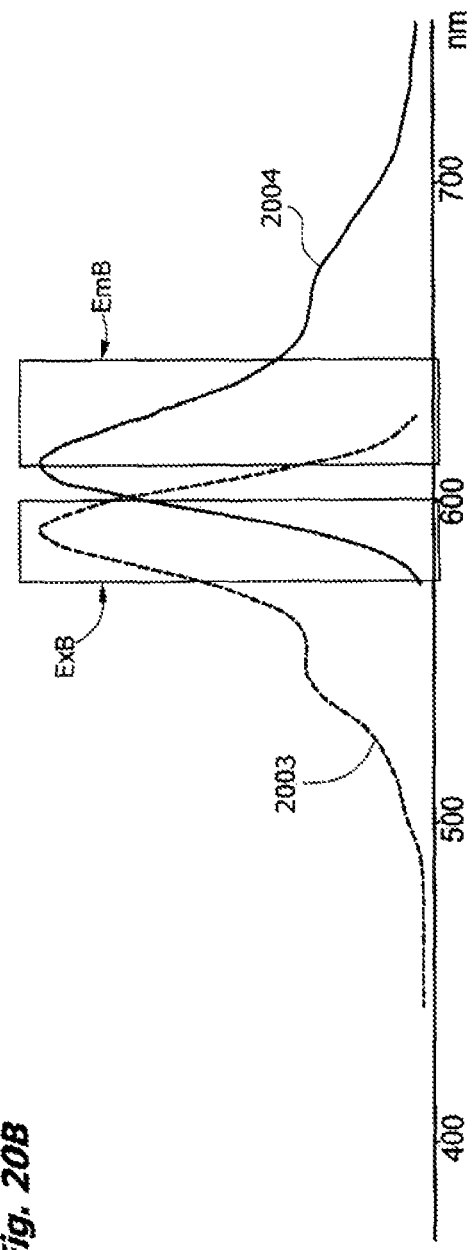

PORTABLE HIGH GAIN FLUORESCENCE DETECTION SYSTEM

CROSS-REFERENCE TO RELATED APPLICATIONS

This application is a continuation of U.S. patent application Ser. No. 13/191,120, filed Jul. 26, 2011, now issued as U.S. Pat. No. 8,329,453, which application is a continuation of International PCT Patent Application No. PCT/US2010/022581, filed Jan. 29, 2010, which application claims the benefit under 35 U.S.C. §119(e) of U.S. Provisional Patent Application No. 61/148,843, filed Jan. 30, 2009, which applications are each incorporated herein by reference in their entireties.

BACKGROUND

1. Field

The present invention relates to a compact fluorescence detection instrument with optics for use in assays performed in a microfluidic cartridge.

2. Description of the Related Art

Although the benefits of the use of fluorophores as probes for in-vitro diagnostic assays are well known, the most commonly available forms of equipment for such assays are large, complex to use, relatively slow and rely on expensive confocal optics. These attributes make much equipment unsuitable for fully integrated "sample-to-answer" testing in remote locales and on-site at the point of care, where such equipment is required to be rugged, fast, compact, inexpensive, and easy to use. Although automated nucleic acid amplification in a microfluidic cartridge was first proposed some years ago (see Wilding, U.S. Pat. Nos. 5,304,487 and 5,635,358), detection of fluorescent assay targets outside controlled laboratory conditions is still hampered by the lack of portable and robust equipment. Two decades since their inception, molecular diagnostics are still relatively uncommon in the absence of advanced laboratory facilities because of these and other unsolved problems.

Needed to promote broader access to molecular diagnostics are self-contained assay systems designed to operate outside specialized laboratory facilities. Nucleic acid assays are rapidly becoming the "gold standard" for the detection of many different disease types, including infectious diseases, because they offer both higher sensitivity and specificity. Such assays have proven highly specific to a broad range of pathogenic conditions and are useful for tracking genetic strains of a particular disease as is fundamental to epidemiology, for example in discriminating H5N1 avian influenza from other types of influenza A or B, in determining whether a particular pathogen target is of a drug-resistant strain or not, and in detecting toxigenic strains of an enteric isolate such as E. coli O157:H7. Fluorescence-based assays have also been shown to be useful for monitoring conditions such as diabetes, cardiopathies, coagulopathies, immunoassays in general, and for detection of endotoxin in foods or drug products for example. Improved equipment is particularly needed for the large numbers of remote health clinics in the developing world where access to health care is limited and many infectious diseases are endemic, and health and life expectancy are poor.

In a typical fluorescence assay system, a fluorescent probe or fluorophore absorbs light having a wavelength or range of wavelengths and becomes excited; and the fluorophore then emits a fluorescent signal. The activity or inactivity of the fluorophore is indicative of the assay result. The emission signal has a wavelength or range of wavelengths that is generally longer than the exciting light (but may be shorter as in "up-converting fluorophores"). A dichroic beam splitter or band-pass filter, or combination thereof, is then used to separate the fluorescent signal from other light, and the signal is passed to a sensor. The sensor is often a photodiode, and generates an electrical signal that can be used to score the assay. Qualitative and quantitative assays using real time or endpoint fluorometry are feasible.

In such systems, a liquid sample is conveyed via a microfluidic channel into a detection chamber or channel of a microfluidic cartridge where a fluorescent probe admixed with or native to the sample is excited by an excitation source. Controls may be run in parallel or multiplexed in the assay channel. Emitted light is measured to determine the presence or absence of a target. A plurality of detection channels may be arranged in the detection region of the microfluidic cartridge. Assays involve making one or more measurements of fluorescence; fluorophores may be used as markers for nucleic acid amplicons formed in an amplification step, or more generally for the presence or absence of a fluorescent assay target. Real time fluorometry, FRET, qPCR, thermal melt curves, kinetic and rate endpoints for assay scoring and validation are also known in the art.

Prior art fluorescence detectors typically employ relatively expensive optical components (such as confocal optics, lasers and aspheric lenses) in order to pick up and localize fluorescent emissions present within a microfluidic cartridge or microarray. WO 98/049543 to Juncosa, for example, teaches three dichroic beam splitters in a single optical train, one for controlling excitation source power and another for controlling reflectance signal; the third dichroic beam splitter is used for discriminating probe-specific fluorescent emission. One or more lenses serve to focus the excitation beam on the sample. Juncosa further teaches use of an aperture at the inlet of a photomultiplier and optical objective lens components of a confocal microscope for controlling an imaging beam with a resolution of "microlocations" at about fifty microns. "By restricting the scope of the illumination to the area of a given microlocation, or a fraction thereof, coupled with restricting the field of view of the detector to the region of illumination, preferably through use of an aperture, significant improvements in signal-to-noise ratio may be achieved." [p 7, lines 10-15]. These teachings are presaged by U.S. Pat. No. 3,013, 467 to Minsky, U.S. Pat. No. 5,296,703 to Tsien, U.S. Pat. No. 5,192,980 to Dixon, U.S. Pat. No. 5,631,734 to Stern, U.S. Pat. No. 5,730,850 to Kambara, and are reiterated in U.S. Pat. Nos. 6,614,030 to Maher and U.S. Pat. No. 6,731,781 to Shams, among others. Maher uses lasers, fiber optics, a quartz plate and aspherical lenses with mini-confocal optical system in order to optimize focusing and emission at a ten micron-sized spot at the center of the microfluidic chamber [Col 3, lines 23-38; Col 7, lines 7-16, 43-48 and 58-63].

Similarly, in U.S. Pat. No. 6,635,487, Lee affirms that focusing the cone of the excitation beam on the plane of the sample "provides the greatest intensity to enhance analytical detection measurements on the assay chips." [Col 1, lines 57-59]. This teaching thus encapsulates the prior art.

In a more recent filing, US Patent Application 2008/0297792 to Kim teaches that an image of an LED serving as a light source for fluorescence detection in a microfluidic chip is projected onto a sample as an "optical spot" by an objective lens. The optical spot is focused at the middle of the depth of a fluid in a chamber in the microfluidic chip [para 0018, 0067, claim 5]. Fluorescence emitted by the sample is collimated as nearly as possible to parallel rays by the objective lens and focused on an avalanche photodiode. The requirement for high precision in alignment relates to the dichroic mirror because the stopband will be shifted for light rays that do not enter the mirror at a 45° angle [para 0071], as is well known. Thus the teachings of Kim reflect the generally recognized state of the art.

In PCT Publication WO2008/101732 to Gruler, where is described a fluorescence detector head for multiplexing multiple excitation and detection wavelengths in a single light path, it is stated that, "A confocal measurement means that the focus of the illumination optics or the source, respectively intrinsically is the same as the focus of the detection optics or sensor, respectively." [p 7, lines 13-16]. Gruler goes on to state, "The confocal optics [of the invention] . . . secures highest signal and lowest background intrinsic features of confocal design" [p 32, lines 1-5], i.e., according to Gruler the highest possible signal and lowest noise are obtained with confocal optics.

While the consensus teaching of the prior art arose out of the specialized use of confocal optics for epifluorescence microscopy, the teaching has been widely and uncritically applied to microfluidic, lateral flow, capillary electrophoresis and microarray applications. However, we have found that this approach is not well suited to liquid phase microfluidic diagnostic assays where detection of one or more molecular probes in a fluid-filled channel is required. Due to effects such as photoquenching, thermo-convection, and the occasional presence of bubbles or gradients in a fluid-filled channel, colocalizing the focal point of the excitation beam and emission cone in the plane of the sample chamber can lead to unacceptable instability, loss of signal, quenching, noise, irreproducibility and overall loss of sensitivity in the results. Because of the higher temperatures of PCR, for example, outgassing of reagents and sample is not an uncommon problem, and interference from bubbles entrained in the liquid sample is a frequent problem. The conventional approach also requires more expensive optical components and thus is disadvantageous for widespread application outside advanced clinical laboratories.

A second problem is assay validation. Current standards for validation of infectious disease assays by PCR, for example, have come to rely on use of spiked nucleic acid templates or more preferably, co-detection of endogenous normal flora, for example ubiquitous non-pathogenic *Escherichia coli* in stools where pathogens such as *Salmonella typhi* or *E. coli* O157 are suspected. Another ubiquitous endogenous template is human 18S rRNA, which is associated with higher quality respiratory and blood samples. Co-amplification and detection of an endogenous template ensures confidence in the assay results but is difficult to achieve in practice because of possible crosstalk between the fluorophores used as markers. When using high gain amplification, some level of crossover in the spectra of the excitation and emission of fluorophores commonly selected for multiplex PCR is typical and expected. Thus a solution that would isolate fluorescent signals with spectrally overlapping shoulders by using separate optical channels within a scanning detector head having shared low-noise electronics for downstream processing would be a technological advance of benefit in the art.

A third problem is portability. Use of disposable cartridges has proved beneficial because cross-contamination due to shared reagent reservoirs and shared fluid-contacting surfaces is avoided. However, configuring a precision optical instrument platform for accepting disposable cartridges is problematic. Problems include inaccuracies and stackup in mechanical tolerances that affect cartridge alignment and detector head positioning, the need for forming a highly conductive thermal interface between the plastic disposable cartridges and heating sources in the instrument, the need for sealing the pneumatic interface between control servos on the apparatus and microvalves on the cartridge, and the necessarily shorter light path available in a microfluidic cartridge (typically about or less than 1 millimeter), which without optimization can lead to loss in sensitivity. A simultaneous solution of these interlocking problems is only achieved by extensive experimentation and development, most often guided by trial and error in this highly unpredictable art. Thus there is a need in the art for numerous improvements, elements of which are the subject of the disclosure herein.

BRIEF SUMMARY

The present invention addresses the problem of reliable and sensitive detection of fluorescent probes, tags, fluorophores and analytes in a microfluidic cartridge in the presence of bubbles and other interfering inhomogeneities in a liquid sample, in a first aspect of the invention, by providing a reflective mirror face formed on a heating block that contactingly interfaces with a thermo-optical window on the underside of the detection channel or chamber containing the liquid sample. The mirror face is formed on the top surface of a heating block and contacts the lower optical window of the detection chamber during use, avoiding the complexity and expense of manufacturing an integral mirror on the bottom of each disposable cartridge, and allowing us to use thinner, more compliant films with lower resistance to heat transfer and transparent optical characteristics for the thermo-optical window of the cartridge. The mirror face is optically flat and polished to improve both heat transfer and fluorescence emission capture. A scanning objective lens is positioned above an upper optical window on the top of the microfluidic cartridge. Excitation light is transmitted through both the upper optical window and the lower thermo-optical window before striking the mirror and reflecting back. Direct and reflected emissions are collected by the objective lens and focused on a detection sensor such as a photodiode, photocell, photovoltaic device, CMOS or CCD chip.

Also, and starkly in contrast to the teachings of the prior art, the problem of fluorescence detection is shown to be solved by configuring the optics so that the excitation optics are decoupled from the emission optics on a common optical path. By trial and error, when using the back mirror, we have found that it is advantageous to place the focal point of the excitation cone near or behind the plane of the reflective mirror and to independently position the emission cone so that emissions are preferentially focused on the detection sensor. Surprisingly, decoupling increases sensitivity, improves limits of detection, and reduces noise or interference of bubbles and other inhomogeneities in the sample.

Contrary to the teachings of the prior art, we find that the conventional confocal localization of the excitation and emission signal is less effective in generating a robust signal over a wide range of sample and operating conditions. Therefore, in one aspect of the invention, it was found that optimization of signal detection may be improved by displacement of the focal point of the excitation light from the plane of the sample to a point behind the sample, a technological advance in the field of low cost optics for use with microfluidic fluorescence assays. Decoupling of excitation and emission optics flies against decades of prior art dedicated to the principles (first espoused by Minsky in U.S. Pat. No. 3,013,467) that form the foundation of conventional practice in confocal microscopy, epifluorescence detection, and microfluidic fluorescence assays. The prior art teachings have lead to the use of aspherical lenses, laser diodes, and precise parfocal alignment of the detection optics with the excitation optics. In contrast, the optics required for delocalized focus of the excitation cone as described here are fortuitously of very low cost and do not require precision assembly or maintenance, as is desirable for manufacturing a low cost, portable instrument.

The mirror face on the top surface of the heating block under the detection chamber is used to increase sensitivity by improving the light-gathering capacity of the objective lens. As the objective lens is placed closer to the detection chamber, a lens of defined angular aperture and numerical aperture becomes more efficient in collecting emissions. Without the back mirror, collection efficiency of a typical system of the prior art is less than 2.5% (assuming for example a 5 mm planoconvex lens). Adding a back mirror can improve this by as much as 200%, and theoretically as much as 400%. And focusing the excitation beam behind the sample chamber can add synergically to any gain in sensitivity by increasing the excitation pathlength by using a mirror. We have found that this is especially advantageous in low aspect ratio microfluidic cartridges, where the optical path length on a z-axis of a cartridge is typically sub-millimeter in length, a significant reduction relative to a standard optical cuvette. Happily, this combination was also found to reduce interferences due to irregularities in the sample chamber such as the presence of small bubbles.

In one embodiment, the mirror is a chromed or polished metal surface on an aluminum or copper heating bock, and is also used to transmit heat or cooling for temperature controlled assays, thus achieving another synergy of design. In a preferred embodiment, the mirror is an electropolished chrome surface on an optically flat aluminum block, the aluminum selected for its superior heat transfer characteristics and scaleable thermal inertia. The block is heated by a resistive heating element in contact with the base of the block. The smoothness and flatness of the mirror face favors optimal heat transfer. In this aspect of the invention, the mirrored face is the upper surface of the heating element used for example for FRET detection or thermal melting analysis of fluorescent probes for PCR amplicons. In one embodiment, a combined application of the optical and thermal properties of the mirror-faced heating block is illustrated by construction of FRET melt curves taken by monitoring fluorescence while ramping the temperature of the assay fluid. In another embodiment, the mirror faced heating block is used to adjust or control a reaction temperature in the detection chamber of a microfluidic card while the cartridge is scanned for fluorescence emission. A mirror-faced heating block for use with microfluidic cartridges in real-time and temperature modulated fluorescence assays demonstrates a technical advance in the art.

According to another aspect of the present invention, we have employed a high gain multi-stage amplifier with noise elimination augmented through the use of downstream signal processing firmware compactly mounted in the scanning head. Very high gain amplification and out-of-plane delocalization of the excitation light cone were found to be synergic in optimizing assay discrimination and sensitivity, even in the presence of bubbles which disrupt specular reflection from the mirror face behind the liquid sample, and happily were implemented with no increase in cost.

The complete optical path uses three lenses, the first for collimating excitation from a light source, the second for projecting the excitation source onto the mirror and for collecting a fluorescent emission from any fluorophore in the sample as collimated emissions, and the third for focusing the emissions on a detector. Each fluorophore is optically isolated by a separate optical channel for measurement. A combination of spectrally-specific LEDs, dichroic mirrors, and barrier filters are used to achieve near monochromatic excitation light in each optical channel. The lenses and related optical components, including the dichroic mirror intersecting the light path for separating excitation and emissions wavelengths and filters, are provided in a guiderail-mounted scanning head that moves laterally across the detection chambers. To minimize noise, the head also includes all electronic components for amplifying the signal and an on-board embedded microprocessor for analog and digital signal processing. Even in the presence of bubble foam interferences that defeat signal averaging and baseline subtraction methods of data acquisition, assay scanning data from each optical channel may be accurately evaluated and reported by conversion to a single bit output (ie. a 1 or a 0). This has been found to be a simple and remarkably effective means for qualitative scoring for the presence or absence of a signal from a particular fluorophore in a liquid sample mixture while the detector head is scanned over the detection chamber or chambers and across the mirror face.

The scanning head and rails are configured with a drive chain coupled to a stepper motor for accurate spatial resolution during scanning. The entire microfluidic cartridge docking bay and optical bench is mounted in an instrument housing at a pitched angle, which we have found advantageous in decreasing bubble entrainment and improving venting during loading, wetout, and mixing operations on the microfluidic cartridge. In a preferred embodiment, the entire optical bench is mounted at an angle of about 15 degrees so that bubbles are displaced from the microfluidic circuitry, necessitating a complete suspension mount for the floating optical bench and the docking bay, and a spring-biased clamping mechanism to ensure active formation of a thermoconductive interface between on-board heating elements mounted in the docking bay on the bottom of the optical bench assembly and the insertable cartridge when the cartridge is loaded into the instrument. A sealed interface between the angled cartridge and a gasketed pneumatic interface port must also be established during docking.

The detector head may be scanned across the detection chamber, or conversely, the microfluidic cartridge may be scanned across the detector. As implemented here, the detector is mounted with a worm gear- or rack and pinion gear-driven stage under control of a stepper motor on twin, paired guiderails. Samples may be scanned on demand by synchronizing data acquisition with motor control; this may be performed using an on-board or external host controller in communication with the embedded microprocessor in the detector head. Surprisingly, such a detector head with integral co-processor, mounted on a linear motion stage for sampling, filtering and averaging measurements on the fly, improved the capability of the system to validate and report assay results despite many potential interferences.

It was expected that there will be variations in fluorescent intensity across the microfluidic chamber, channel or detection field, which can be several millimeters in width. These variations arise, for example, as a result of inhomogeneities in mixing, from differences in well thickness, from imperfections in the optical windows, from small temperature variations across a heated detection well (which can cause accompanying variations in hybridization-dependent fluorescence of amplicons being detected, for example) and from bubbles or foam which arise from degassing and mixing. It was found that these variations can be minimized by signal digitization over a sampling transect across the detection chamber using a threshold to discriminate positive and negative test results.

In order to further provide noise elimination, extraneous noise is removed by strobing the excitation beam at a frequency known to prevent interference by AC line fluctuations and other ambient electric or RF interference; resulting in cleaner signal modulation, a modulated signal that also can be filtered to remove the effects of any ambient light leaking into the instrument housing. We have achieved this result by configuring the optics printed circuit board with a dedicated co-processor, and using independent clock frequency and firmware, which efficiently minimizes traffic on a databus connected to the host instrument. The on-board optical signal processor has dedicated instructions stored in EEPROM resident on the optics card, and synchronizes pulses sent to the source LED with interrogation of the sensor photodiode at a frequency selected to limit electromagnetic interference. The firmware is designed to evaluate the difference in signal between strobe illumination bursts of excitation light and background between strobe bursts, and any background due to ambient or extraneous light is readily subtracted by this method.

The resulting optics modules are packaged in a sealed detector housing and can be expanded as a series of optics modules with multiple optical channels for simultaneously scanning multiple samples or fluorophores in series or in parallel. Signal processing is routed to a single co-processor embedded in the detector head, and from there to the host instrument controller. Thus the invention comprises single head/single channel embodiments, dual head/dual channel embodiments, and multi-head/multichannel embodiments and may perform single and multiplex assays on single samples or on multiple samples in parallel.

The detectors were found to function well when housed as dual head and multi-head detectors, where two or more channels in a single housing were configured with fully independent optics, fluorophore-specific filters, dichroic mirrors and source LEDs, reducing crosstalk between multiple fluorophores. The head thus will optionally contain a plurality of light sources mounted on a first circuit board and a plurality of objective lens and associated detectors mounted on a second circuit board, and will collect signals for each of a plurality of fluorophores independently using shared signal processing capability and firmware embedded in the detector head. To reduce noise, no analog signals are transmitted from the detector head to the host instrument.

In this way, light sources for excitation in each channel can be matched to the individual fluorophores. It is no longer necessary to provide white light and an excitation filter to ensure a narrow pass beam of excitation light striking the sample. This simplification proved useful in assay protocols calling for paired collection of "biplex" or multiplex target and control signals. Where, as for FDA CLIA waiver requirements, both target and control templates are amplified in parallel, a positive control signal must be present before an assay result on a test sample can be reported or billed. In the absence of a detectable control signal, any target signal detected is not a valid result. In order to meet CLIA waiver requirements, it is necessary that the fluorescence detector be able to detect not only the presence, for example, of a target infectious organism amplified by PCR but also of an endogenous human control organism co-existing with the target and amplified by the same PCR reaction or a PCR reaction conducted in parallel in the instrument, for example.

Such an approach requires that the fluorescent detector have the capacity to determine the presence of both the target and the control fluorophores as a "biplex" ("duplex") amplification reaction mixture in a common detection chamber. A positive amplification control fluorophore is typically used which has fluorescent excitation and emission spectra which is shifted (in wavelength) so as to be well resolved by selective band pass filters from the fluorescent excitation and emission spectra for the target fluorophore (see FIG. 7 for example). However, according to the present invention, it proved possible to achieve superior resolution by using a dual head detector and by scanning each detection chamber twice in series, once with each optical channel, detecting first the control fluorescence signature, then the test sample fluorescence signature—each scanning pass utilizing separate excitation and emission optics as described above.

A benefit was found by configuring these detectors with fully separated and independent light paths. In this aspect of the invention, the use of a duplex head design ensures that the presence of an amplification control fluorophore in a sample does not inadvertently create a signal in the target channel due to "crosstalk". Such a situation would result in the sample being classed as a "false positive". Conversely, it is also important that there is no crosstalk from the target channel to the control channel, which is likely when multiple signals share a common optical path. Such a situation could result in the positive amplification control being inadvertently deemed present, when this may not be the case, and would lead to reporting of an invalid assay, an unacceptable outcome.

These principles are exemplified by the use of fluorescein or equivalent fluorophore as a molecular probe for the target, and Texas Red or equivalent fluorophores as a molecular probe for the control. A dual head detector, with one detection channel optimized for detection of fluorescein and the other detection channel optimized for Texas Red, each with separate excitation and detection optics, was found to be surprisingly sensitive, accurate and robust. The detector head was moved so as to position each optical channel in turn over the sample and separate fluorescence readings were made. Surprisingly, this improved resolution and minimized cross talk but did not contribute to higher noise or loss of sensitivity due to the mechanics of moving the head. Because excitation is not performed with white light, but is instead performed at a wavelength specific for an individual fluorophore, quenching of the second fluorophore is not an issue.

In another aspect of the invention, we have found that multiple microfluidic channels can be scanned by sequential traverse of a multihead detector across multiple sample wells, each head being configured with independent optics for excitation and emission of a single fluorophore. Although the excitation and detection optics are separated for each optical channel, signal processing is performed in circuitry shared within the detector head.

Thus in yet another embodiment the invention provides a robust multi-head independent channel fluorescent detection system for a point of care molecular diagnostic assay which has a high degree of specificity directed towards the presence of both a target and an nucleic acid amplification control co-existing in a common or parallel detection chamber. The cleaner signals permit higher gain electronic amplification without a corresponding decrease in signal-to-noise ratio. Although a first embodiment in this invention describes a dual channel detector (for the presence of a single target and a control), the invention may also be applied to a fluorescent detection system having more than two channels, for example to detect a multiplex of targets and a control co-existing in a single detection chamber. Optionally, the heads may be positioned side-by-side, in an array, or radially, as in a cylinder.

Use of the independent optical pathways fortuitously resulted in reduced need for precision in assembly of lenses, dichroic beam splitters, and associated filter elements, improving the manufacturability of the apparatus. Embodiments of the present invention incorporate inexpensive non-precision optics, plastic lenses, a mirror on the heating block behind the sample window, moveable stage elements, strobed excitation and emission, noise suppression, on-board continuous signal processing over a movable detection field, and more than one optical channel for biplex assay validation by use of paired target and control fluorophores. Despite its high amplification gain, the instrument has proven advantageously resistant to interferences such as electrical noise and bubbles in the detection chamber.

BRIEF DESCRIPTION OF THE DRAWINGS

FIG. 2 is an animated view showing the insertion of the microfluidic cartridge in the docking bay.

FIG. 8B illustrates the worm drive operation on the clamping gear rack.

FIG. 9B illustrates the worm drive operation of the clamping gear rack and the platen arm.

FIGS. 20A and 20B show emission and excitation wavelengths for two fluorophores in a liquid sample, and illustrate dual head optical isolation for removal of crosstalk.

DETAILED DESCRIPTION

Figure 1:
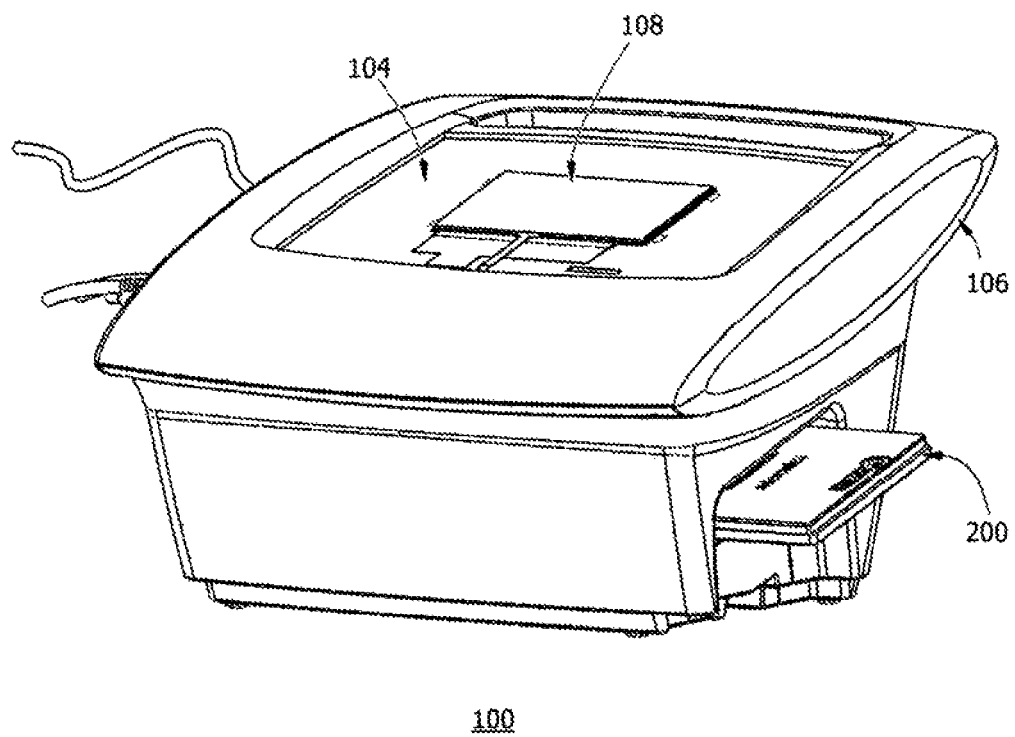
FIG. 1 is a perspective view of an instrument of the invention and a microfluidic cartridge in the docking bay.

Although the following detailed description contains specific details for the purposes of illustration, one of skill in the art will appreciate that many variations and alterations to the following details are within the scope of the claimed invention. The following definitions are set forth as an aid in explaining the invention as claimed.

Definitions

"Angular aperture"—is the angle between the most divergent rays from a single point that can enter the objective lens and participate in image formation.

"Back focal length"—is defined for a lens with an incident beam of collimated light entering the lens as the distance L from the back surface of the lens to the focal point of a cone of focused light. "Back focal positions" indicates that non-collimated rays may be focused at alternate distances from the back of the lens by decoupling the optics.

Target analyte: or "analyte of interest", or "target molecule", may include a nucleic acid, a protein, an antigen, an antibody, a carbohydrate, a cell component, a lipid, a receptor ligand, a small molecule such as a drug, and so forth. Target nucleic acids include genes, portions of genes, regulatory sequences of genes, mRNAs, rRNAs, tRNAs, siRNAs, cDNA and may be single stranded, double stranded or triple stranded. Some nucleic acid targets have polymorphisms, deletions and alternate splice sequences. Multiple target domains may exist in a single molecule, for example an immunogen may include multiple antigenic determinants. An antibody includes variable regions, constant regions, and the Fc region, which is of value in immobilizing antibodies. Target analytes are not generally provided with the cartridge as manufactured, but are contained in the liquid sample to be assayed; in contrast, "control analytes" are typically provided with the cartridge and are assayed in order to ensure proper performance of the assay. Spiked samples containing target assay may be used in certain quality control testing and for calibration, as is well known in the art.

Means for Amplifying: The grandfather technique was the polymerase chain reaction (referred to as PCR) which is described in detail in U.S. Pat. Nos. 4,683,195, 4,683,202 and 4,800,159, Ausubel et al. Current Protocols in Molecular Biology, John Wiley and Sons, Baltimore, Md. (1989), and in Innis et al., ("PCR Protocols", Academic Press, Inc., San Diego Calif., 1990). Polymerase chain reaction methodologies require thermocycling and are well known in the art. Briefly, in PCR, two primer sequences are prepared that are complementary to regions on opposite complementary strands of a target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the marker sequence by adding on nucleotides. By raising and lowering the temperature of the reaction mixture, the extended primers will dissociate from the template to form reaction products, excess primers will bind to the template and to the reaction products and the process is repeated. By adding fluorescent intercalating agents, PCR products can be detected in real time.

Other amplification protocols include LAMP (loop-mediated isothermal amplification of DNA) reverse transcription polymerase chain reaction (RT-PCR), ligase chain reaction ("LCR"), transcription-based amplification systems (TAS), including nucleic acid sequence based amplification (NASBA), "Rolling Circle", "RACE" and "one-sided PCR", also termed "asymmetrical PCR" may also be used, having the advantage that the strand complementary to a detectable probe is synthesized in excess.

These various non-PCR amplification protocols have various advantages in diagnostic assays, but PCR remains the workhorse in the molecular biology laboratory and in clinical diagnostics. Embodiments disclosed here for microfluidic PCR should be considered representative and exemplary of a general class of microfluidic devices capable of executing one or various amplification protocols.

Typically, nucleic acid amplification or extension involves mixing one or more target nucleic acids which can have different sequences with a "master mix" containing the reaction components for performing the amplification reaction and subjecting this reaction mixture to temperature conditions that allow for the amplification of the target nucleic acid. The reaction components in the master mix can include a buffer which regulates the pH of the reaction mixture, one or more of the natural nucleotides (corresponding to A, C, G, and T or U—often present in equal concentrations), that provide the energy and nucleotides necessary for the synthesis of nucleic acids, primers or primer pairs that bind to the template in order to facilitate the initiation of nucleic acid synthesis and a polymerase that adds the nucleotides to the complementary nucleic acid strand being synthesized. However, means for amplication also include the use of modified or "non-standard" or "non-natural" bases such as described in U.S. Pat. No. 7,514,212 to Prudent and U.S. Pat. Nos. 7,517,651 and 7,541,147 to Marshall as an aid to detecting a nucleic acid target.

Means for detection: as used herein, refers to an apparatus for displaying an endpoint, ie. the result of an assay, and may include an instrument equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Magnifying lenses in the cover plate, optical filters, colored fluids and labelled probes may be used to improve detection and interpretation of assay results. "Labels" or "tags" include, but not limited to, dyes such as chromophores and fluorophores; and chemoluminescence as is known in the prior art. QDots, such as CdSe coated with ZnS, decorated on magnetic beads, or amalgamations of QDots and paramagnetic $Fe_3O_4$ microparticles, are a convenient method of improving the sensitivity of an assay of the present invention. Fluorescence quenching detection endpoints are also anticipated. A variety of substrate and product chromophores associated with enzyme-linked immunoassays are also well known in the art and provide a means for amplifying a detection signal so as to improve the sensitivity of the assay, for example "up-converting" fluorophores. Fluorescence and optical detectors may include photodiodes, photovoltaic devices, phototransistors, avalanche photodiodes, photoresistors, CMOS, CCD, CIDs (charge injection devices), photomultipliers, and reverse biased LEDs. Detection systems are optionally qualitative, quantitative or semi-quantitative.

"Molecular beacon"—is a single stranded hairpin-shaped oligonucleotide probe designed to report the presence of specific nucleic acids in a solution. A molecular beacon consists of four components; a stem, hairpin loop, end-labelled fluorophore and opposite end-labelled quencher. When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. 'Wavelength-shifting Molecular Beacons' incorporate an additional harvester fluorophore enabling the fluorophore to emit more strongly. Current reviews of molecular beacons include Wang K et al, 2009, Molecular engineering of DNA:molecular beacons. Angew Chem Int Ed Engl, 48(5):856-870; Cissell K A et al, 2009, Resonance energy transfer methods of RNA detection, Anal Bioanal Chem 393(1):125-35 and Li Y, et al, 2008, Molecular Beacons: an optimal multifunctional biological probe, Biochem Biophys Res Comm 373(4):457-61. Recent advances include Cady N C, 2009, Quantum dot molecular beacons for DNA detection. Methods Mol Biol 554:367-79.

Fluorescence nucleic acid assays include amplification with tagged primers and probe-based detection chemistries. Fluorescent products can be assayed at the end of the assay, or by measuring the amount of amplified product in real time. While not limiting, TaqMan Probe (Applied Biosystems) which relies on displacement and polymerase-mediated hydrolysis of a 5' reporter dye with 3' quencher construct, FRET hybridization probes, dual oligo FRET-based probes (Roche), minor groove binder-conjugated hybridization probes (MGB probes, Applied Biosystems), Eclipse probes, Locked NA Probes (Exiqon/Roche), Amplifluor primer chemistries, Scorpions primer chemistries, LUX primers, Qzyme primers, RT-PCR, among others, are all suitable in the present invention. Intercalation dyes may also be used. Reverse transcriptase is used to analyze RNA targets and requires a separate step to form cDNA. Recent advances include Krasnoperov L N et al. 2010. Luminescent probes for ultrasensitive detection of nucleic acids. Bioconjug Chem 2010 Jan. 19 epub.

In addition to chemical dyes, probes include green fluorescent proteins, quantum dots, and nanodots, all of which are fluorescent. Molecules such as nucleic acids and antibodies, and other molecules having affinity for an assay target, may be tagged with a fluorophore to form a probe useful in fluorescent assays of the invention.

"FRET" (Fluorescence Resonance Energy Transfer)—is a fluorescence technique that enables investigation of molecular interactions. It depends on the transfer of energy from one fluorophore to another fluorophore (ie. a donor and a quencher) when the two molecules are in close proximity such a when hybridized. Recent advances include Carmona A K et al, 2009, The use of fluorescence resonance energy transfer (FRET) peptides for measurement of clinically important proteolytic enzymes, An Acad Bras Cienc 81(3): 381-92.

Unless the context requires otherwise, throughout the specification and claims which follow, the word "comprise" and variations thereof, such as, "comprises" and "comprising" are to be construed in an open, inclusive sense, that is as "including, but not limited to". Reference throughout this specification to "one embodiment", "an embodiment", "one aspect", or "an aspect" means that a particular feature, structure or characteristic described in connection with the embodiment or aspect may be included one embodiment but not necessarily all embodiments of the invention. Furthermore, the features, structures, or characteristics of the invention disclosed here may be combined in any suitable manner in one or more embodiments. "Conventional" is a term designating that which is known in the prior art to which this invention relates. "About" and "generally" are broadening expressions of inexactitude, describing a condition of being "more or less", "approximately", or "almost" in the sense of "just about", where variation would be insignificant, obvious, or of equivalent utility or function, and further indicating the existence of obvious minor exceptions to a norm, rule or limit.

"Crosstalk"—in fluorescence imaging occurs when the excitation and/or emission spectra of two or more fluorophores (and/or autofluorescence) in a specimen overlap, making it difficult to isolate the activity of one fluorophore alone.

Turning now to the figures, FIG. 1 is a perspective view of the instrument 100 with a microfluidic cartridge 200 in the docking bay. Shown are membrane panel 104 and touch screen display surfaces 108 and compact chassis or housing 106. Because all reagents are provided in the microfluidic cartridge, the instrument has full standalone operability. FIG. 2 complements this exterior view by animating the insertion of the microfluidic cartridge anterior nose 105 into the docking bay 103. The docking bay is suspension-mounted and tilted at an angle relative to the instrument base, as will be discussed in more detail below.

The angled, tilted, floating stage with on-board optical bench and docking bay is a distinctive feature of the instrument. This feature is introduced conceptually in FIG. 3. A tilt sensor may be used in conjunction with the instrument host controller in order to ensure the proper angle is maintained for improved performance. The mounting angle of the inclined mounting plate determines the angle at which the microfluidic cartridge is held during the assay. This angle "theta" has been found to be advantageous in the range of 10-45 degrees from the ground plane, more preferably 10-20 degrees, and is most preferentially about 15 degrees. The angular mount has been found to relieve bubble interference that may be associated with deterioration in PCR amplification results, a technological advance in the art.

Figure 3A:
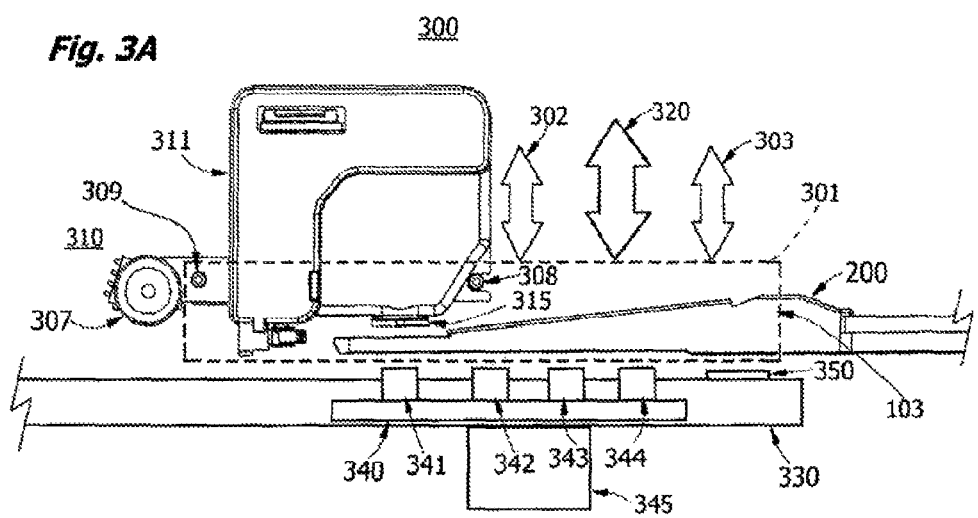
FIG. 3A is a simplified representation of a floating stage with docking bay, optical bench, and clamping mechanism for thermally contacting the microfluidic cartridge with the heating module and scanning the microfluidic cartridge.

FIG. 3A is a schematic diagram of the primary optothermomechanical subsystems of the instrument. The floating stage 300 consists of a tray-like chassis 301 that is suspended on an inclined plane by a four-point spring-mounted suspension (indicated by 302,303) and supports a docking bay 103 for receiving a microfluidic cartridge 200 and scanning detector head 311 mounted on paired guiderails (308,309). The cartridge is not part of the instrument 100, but interfaces with the instrument after insertion into the floating docking bay 103.

During operation, the floating stage is clamped (indicated by 320) against inclined mounting plate (330) and engages contacting surfaces of zone heating blocks (341,342,343,344) of a heating module 340 and associated resistive heating elements and circuits. A fan 345 is provided to dissipate excess heat during cooling. The inclined mounting plate is also provided with a pneumatic interface port 350 for sealedly docking to the base of the microfluidic cartridge. Pneumatic pressure is delivered to the cartridge through the pneumatic interface port from an integral pneumatic distribution "manifold" or system embedded in the inclined mounting plate 330. The pneumatic manifold supplies negative and positive pressure from sources mounted on the inclined mounting plate. A motherboard-mounted, programmable host controller directs pneumatic driving pressure, vacuum, and control pulses to pumps and valves on the cartridge via the internal manifold in the base plate 330 and pneumatic interface port 350.

The detector head is motorized and scanning of the cartridge is performed under the control of the central host controller. To scan the detector head along paired guiderails (308,309) the host controller engages a worm-gear driven by stepper motor 307. The detector head is fitted with an external window with objective lens 315 which scans optical windows in the anterior nose 105 of the microfluidic cartridge and collects raw optical signals. The detector head has its own embedded microprocessor as described in FIGS. 10 and 18. The programmable host controller also regulates temperature in one or more heating elements in the heating module and a set of solenoid valves and positive pressure and vacuum pump reservoirs linked to the pneumatic interface. The instrument is supplied with a display panel and touch panel for user interactions. Power input is flexible, and is optionally supplied by an AC adaptor, car adaptor, or from a rechargeable battery mounted under the instrument. Also included are optional wireless IO and digital IO ports.

Figure 3B:
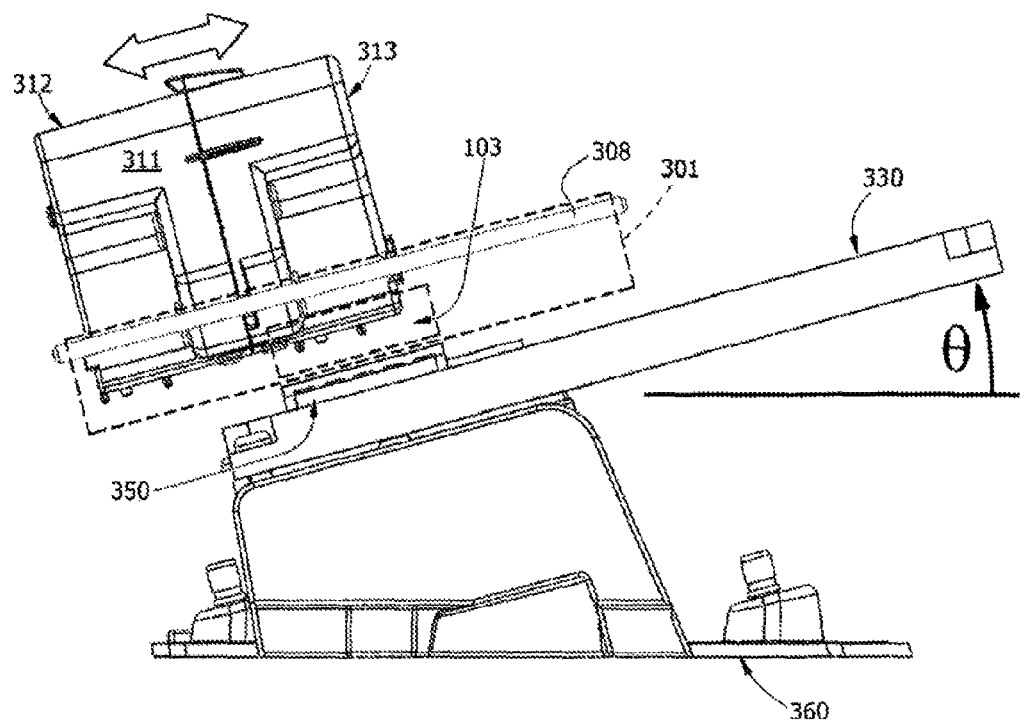
FIG. 3B demonstrates conceptually that the floating stage, docking bay, optical bench and microfluidic cartridge are mounted in the instrument chassis at a defined angle "theta" relative to the ground plane, where the ground plane is horizontal.

FIG. 3B demonstrates conceptually that the floating stage 301, docking bay 103, detector head 311, and microfluidic cartridge 200 are mounted in the instrument chassis 106 at a defined angle relative to the ground plane. Tilting the cartridge at an angle from the ground plane improves venting during fluid loading and minimizes air entrainment during wetting and mixing operations. Bubble accumulation, which interferes with heat transfer and optical interrogation of assay results, is avoided by this and other innovations disclosed here. The inclined mounting plate 330 establishes the angle of the floating stage 301, cartridge 200, and mechanical components of the clamping 800 and optical scanning 310 subassemblies. We also found that bubble accumulation interfered with nucleic acid amplification, and was limited by the angular mount of the stage.

As shown in FIG. 3B, the detector head is mounted in a clamshell housing with mating half shells (312,313). The detector head slides on lateral guide rails 308 and 309 and is under host control of a stepper motor 307 with worm drive. The floating stage chassis 301 is springedly mounted in a four-point suspension and has no direct connection to the inclined mounting plate 330 until clamped. The clamping mechanism is indicated here figuratively by an arrow 320 and will be discussed in more detail below. All mechanical components of the clamping mechanism are attached to the inclined mounting plate so that the entire docking bay and clamping mechanism are rotated at a fixed angle theta from the ground plane.

One of the two scanning guiderails 308 is readily visible in this view, and is supported at either end by the floating stage chassis or tray 301. The docking bay (103) is indicated by a dotted line and marks the opening for insertion of the nose of the microfluidic cartridge under the detector head 311, which scans from side to side as shown (double arrow). The pneumatic interface port 350, shown here as a raised platform under the docking bay, obscures the position of the heating module 340 and heating blocks 341-344 immediately inferior and in line with the docking bay. Power conditioning, AC adaptors and battery storage functions are mounted beneath the inclined mounting plate 330 above the underside of the 360, which is designed to rest on a flat surface.

Figure 4A:
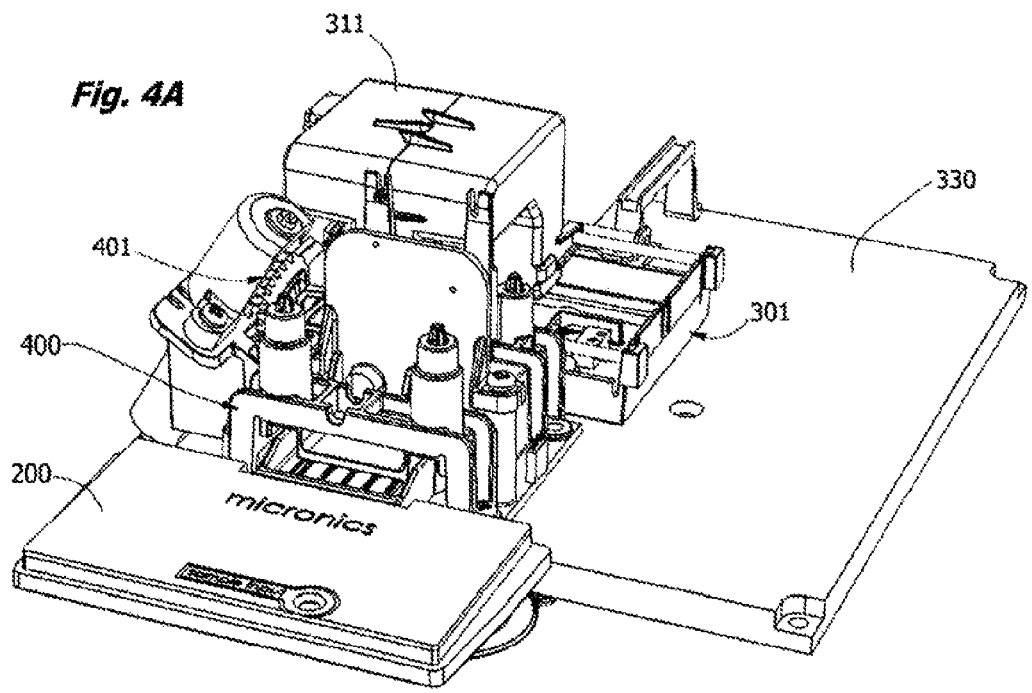
FIGS. 4A and 4B are front and rear interior perspective views from above, showing the suspension-mounted stage with docking bay, optical bench, and scanning detector head.
Figure 4B:
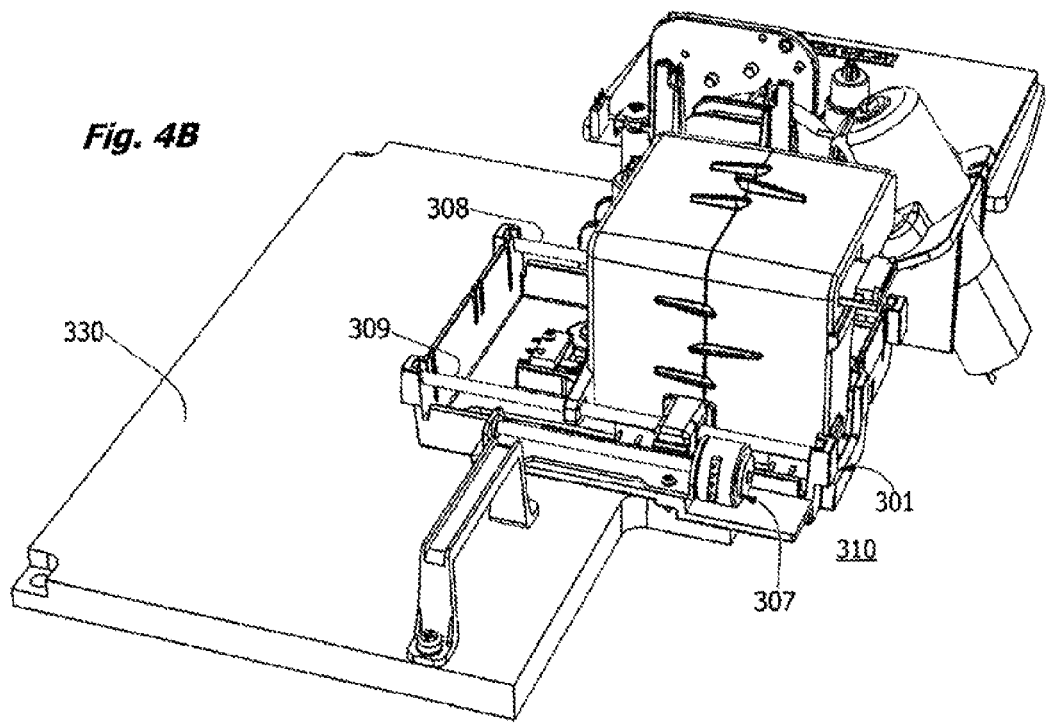

FIGS. 4A and 4B are front and rear interior CAD views from above, showing the suspension-mounted stage with floating chassis 301 with optical bench and detector head 311, and docking bay occupied by a microfluidic cartridge 200. The floating stage is suspended from a saddle shaped support, docking saddle 400, which is rigidly bolted to the inclined mounting plate 330. Also shown is a gear rack 401 that provides clamping pressure, as will be described in more detail below. In FIG. 4B, the guiderails (308,309) and stepper motor 307 of the optical bench are readily recognized. The inclined mounting plate 330 is populated with pumps, vacuum and pressure storage tanks, solenoids and pneumatic control circuitry (not shown), but will not be described in detail here.

Figure 5A:
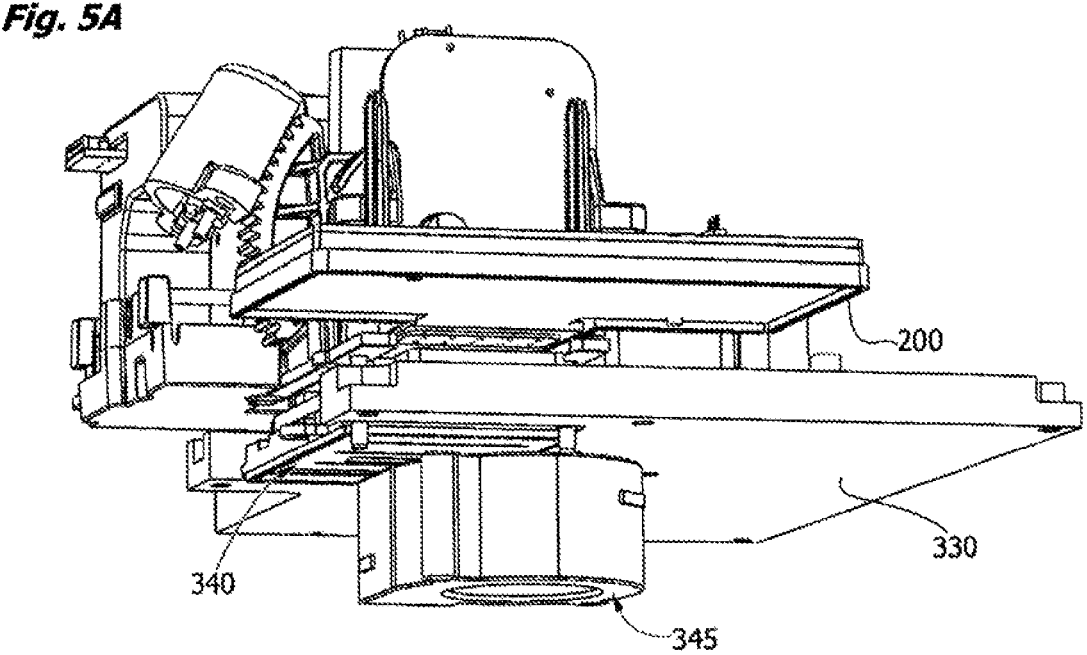
FIG. 5A is a front interior perspective view from below the docking bay, showing the underside heating module and cooling fan.

FIG. 5A is a front interior perspective view from below the docking bay, showing the underside heating module 340 and cooling fan 345. It can be seen that on insertion of the microfluidic cartridge 200 into the docking bay, the heating module 340 is brought into alignment with the underside of the cartridge.

Figure 5B:
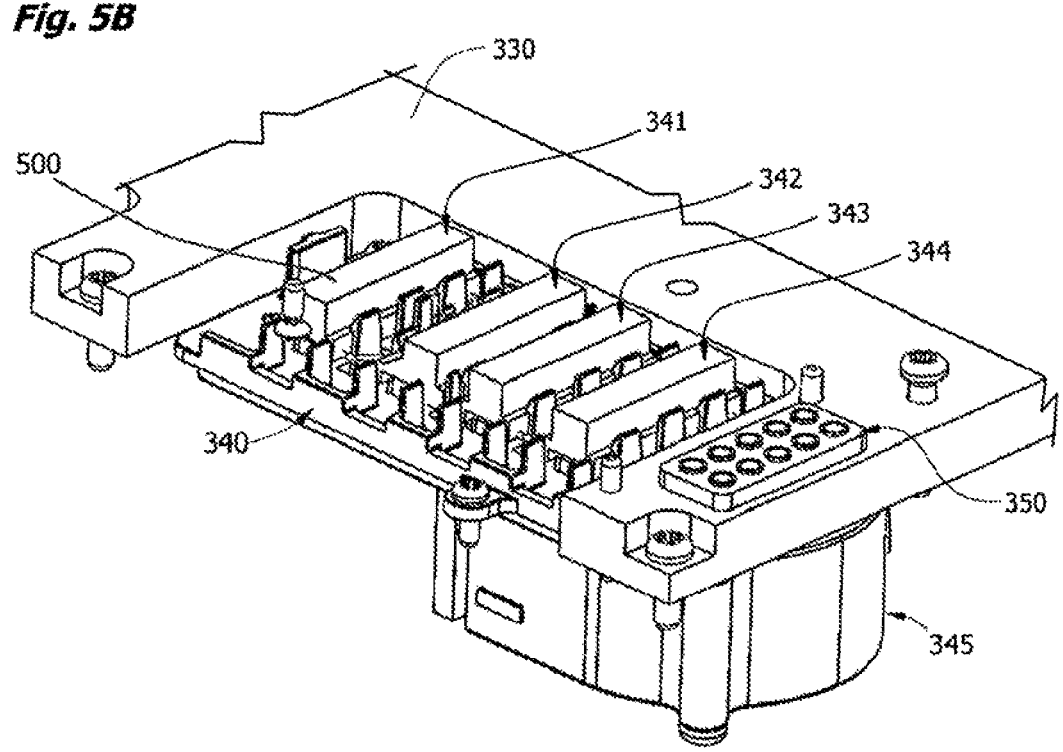
FIG. 5B is a detail of the heating module with heating block elements and mirror face.

FIG. 5B is a detail of the heating module 340 with heating block elements ("thermal elements" 341,342, 343,344) and mirror face (500). The superior aspect of the heating module consists of one or more heating blocks, each of which forms a thermal interface with a defined zone on the underside of the microfluidic cartridge for proper operation of the biochemical or molecular biological reactions that occur in the enclosed channels and chambers of the cartridge during the assay. These reactions can be as simple as immunobinding or hybridization, or as complex as nucleic acid amplification or enzymatic dehydrogenation coupled to the formation or consumption of nicotinamide adenine dinucleotide and adenosine triphosphate, or cascading clotting factors, and generally require relatively stringent temperature control for optimal reactivity and specificity. The heating blocks (341,342,343, 344, although the invention is not limited to this configuration) may be spring-mounted and are urged upward in opposition to the downward pressure of the clamping mechanism so as to establish high thermal diffusivity contact zone for heat transfer. Each heating block is in thermal contact with a resistive (Coulombic) heating element, generally by means of a compliant thermal pad for good thermal conductivity. Each heating block contacts a thermal window in the microfluidic cartridge. Each window is generally a thin layer of a flexible plastic film, may be less than 3 mils in thickness, and most commonly of a compliant transparent material such as polyethylene terephthalate (Mylar®), although optionally of a cyclic polyolefin or polyimide with good optical transparency, while not limited thereto (see U.S. Pat. No. 7,416,892, which is co-assigned), and also having good thermal conductivity. Thus in one embodiment the invention is a thermo-optical interface for reflective transillumination of a detection chamber in a microfluidic card while controlling or modulating the temperature of a liquid sample in the detection chamber. This feature is of benefit for performing a reaction or reactions associated with an analyte while monitoring an optical signal associated with the analyte. In one exemplary application, thermal melt curves are used to verify FRET hybridization results.

Also shown is the fan housing 345, which is used to dissipate heat from heat sinks below the heating blocks and in PID control of temperature in the blocks in combination with resistance heating circuits (not shown).

Heating block 341 in this case is modified by fabrication with a polished chromium mirror face 500 on the upper aspect which contacts and aligns with thermo-optical windows in the microfluidic card 200 during the assay. The thermo-optical window in this case corresponds to a detection chamber enclosed in the cartridge body. The mirror face reflects light from the detector head 311, which scanningly transilluminates the cartridge, back into the objective lens 315, and also reflects any fluorescent emission from the cartridge detection chambers back into the detector head and from there to the detection sensor, which is typically a photodiode, as will be discussed in more detail below. Heating block 341 in this example differs from the other heating blocks, and is generally machined from aluminum, then polished and coated with an underlayer of copper under nickel before application of the chromium mirror face. Electropolishing and/or buffing may be used to form a highly reflective optical finish on the chrome surface. The optically flat superior surface of the block aids in heat transfer and improves sensitivity of fluorescence assays. Happily, the use of the mirror permits simultaneous heating and optical interrogation of the fluid contents of the detection chamber, as is useful for example in optically assaying melting curves.

Other heating zones may be modified similarly to permit optical monitoring with simultaneous temperature control or modulation. The configuration of heating zones and mirrors may be modified or adapted for particular assay/cartridge requirements, and is not limited to the configuration shown here.

FIG. 5B also shows pneumatic interface port 350, here with ten outlets, each independently ported to a source of positive or negative pressure from the pneumatic distribution manifold of the host instrument and independently under the control of a programmable host controller. These outlets interface and seal to mated inlets in the underside of the microfluidic card, and a timed pattern of intercommunicating pneumatic pressure, vacuum and pressure pulses are routed through the pneumatic interface to drive and control the assay in the cartridge.

Figure 6A:
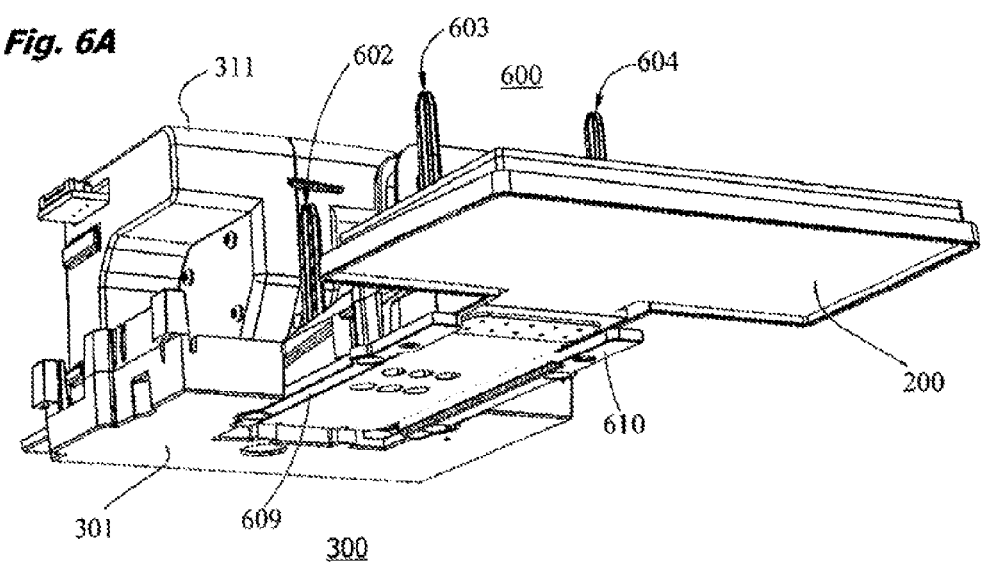
FIGS. 6A and 6B are perspective views of the floating stage with insertable cartridge in place in the docking bay. For clarity, the docking saddle and accessory mounting elements have been removed.
Figure 6B:
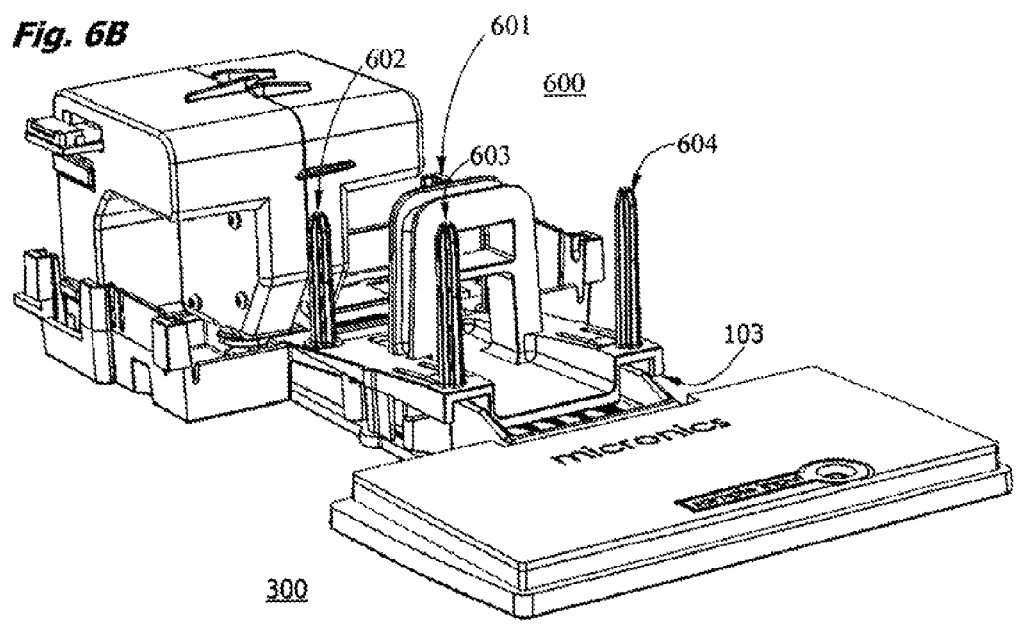

FIGS. 6A and 6B are perspective views of the floating stage subassembly 300 with insertable cartridge in place in the docking bay 103. For clarity, the docking saddle 400 and accessory mounting elements have been removed. It can be seen in FIG. 6A how the inferior surface of the microfluidic cartridge 200 is shaped to be contacted with the mated superior surfaces of the heating module 340 of FIG. 5B. The cartridge is secured and supported under the floating stage 301 by two attached lateral flanges 609 and 610, which are bolted in place and guide insertion.

In FIG. 6B, four vertical posts (601,602,603,604) forming the male elements of the four-point suspension 600 are apparent on the anterior section of the floating stage 300. These posts are fitted with coil springs (603a in FIG. 7) and inserted into cylindrical suspension housings (605, 606,607,608 in FIG. 7) formed with in the docking saddle 400. They serve to suspend the floating stage 300 and optical scanning assembly as will be described in more detail in the next figure, FIG. 7. The entire optics bench and docking bay subassembly shown in FIGS. 6A and 6B floats on this suspension and is rigidly brought into contact with the rest of the instrument only on downward action of the clamping mechanism as will be shown in FIGS. 8 and 9.

Figure 7:
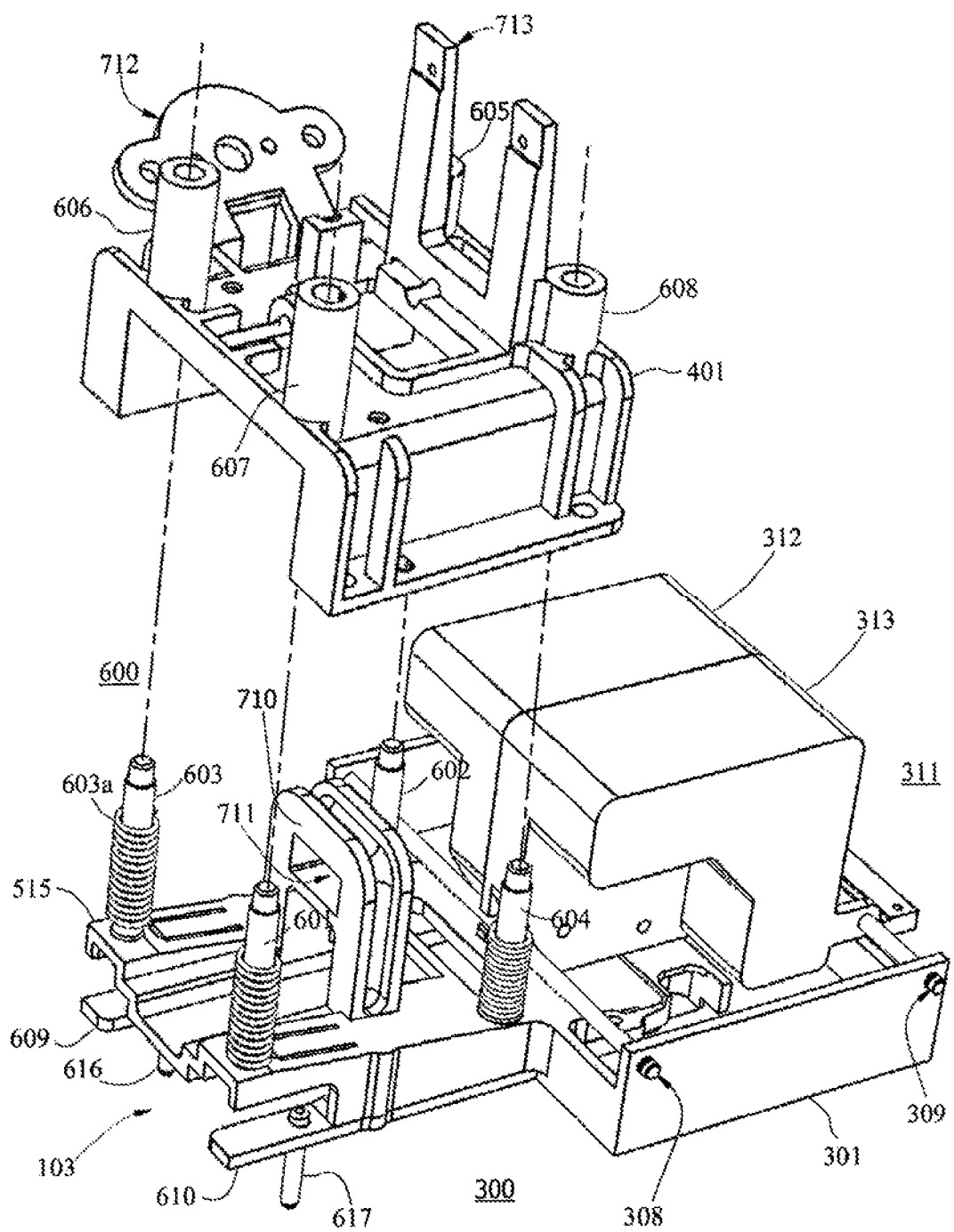
FIG. 7 is a detailed view of the docking bay and floating stage suspended from the underside of the docking saddle. The floating stage is fitted with a four point spring suspension.

FIG. 7 is an exploded view of the floating stage 300 with detector head 311 docking bay 103 suspended from the underside of the docking saddle 400. The floating stage is fitted with a four point spring suspension with coil springs (replicates of 603*a*) on each of the four supporting posts (601,602,603,604). Each post is received in a mated suspension housing (605,606,607,608) of the docking saddle. The microfluidic cartridge 200 is not shown, but it can be seen in this view that the docking bay is configured for receiving the nose of the cartridge at the projecting nose 515 of the docking bay, so that the cartridge rests on lower lateral flanges (609, 610). Alignment pins (616,617) ensure that the docking bay seats true when pressed down against the heating module 340. The posterior section of the floating stage, which contains the guiderails (308,309) and detector head 311 for fluorescence scanning, is free of any support other then at the docking saddle and is cantilevered from the docking saddle during operation. The role of guiderails (308,309) in supporting motion of the scanning detector head 311 is apparent in this view.

The docking saddle is provided with brackets 712 and 713 for attaching the clamping mechanism 800 as will be discussed below, and bar code readers as are useful in automated operation. Linker arm 710 with slot 711 is engaged by the clamping gear mechanism as discussed below and the floating stage 300 raised or lowered as a single assembly. Docking saddle 400 and linker arm 710 also operatively fix the floating stage at the theta angle of the inclined mounting plate.

Figure 8A:
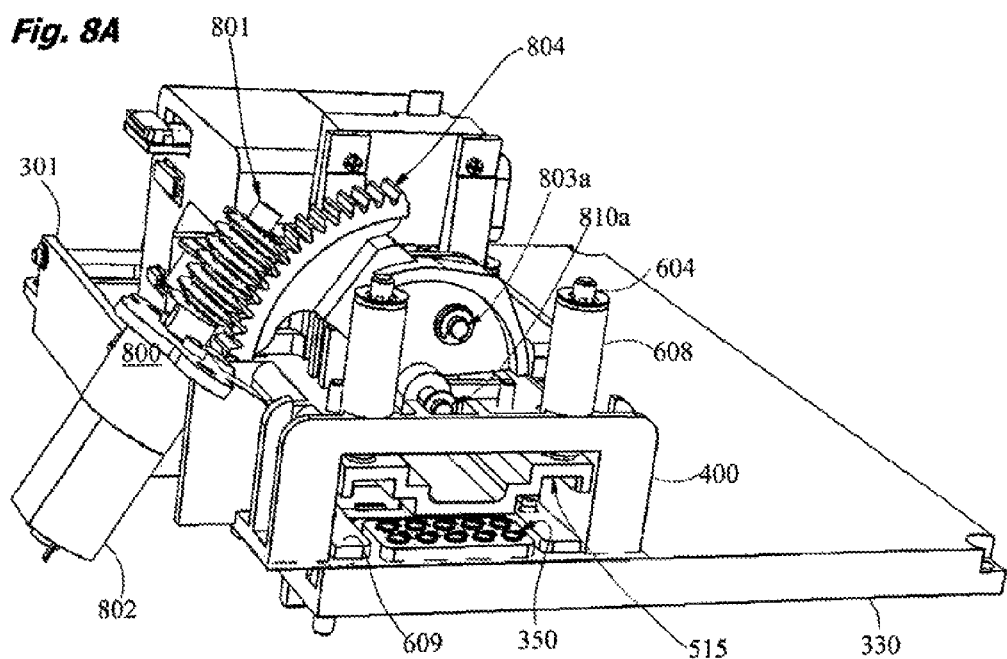
FIGS. 8A and 8B are anterior subassembly views of the clamping mechanism.

FIG. 8A is a frontal view of the clamping mechanism. The bridging shape of the docking saddle 400 is seen to rest above the anterior nose 515 of the floating docking bay 103. Immediately under the docking bay mouth is the pneumatic interface port 350, visible between lateral flanges 609 and 610 forming the channel for receiving the microfluidic cartridge 200. During docking of the loaded cartridge, the function of the clamping mechanism is to urge the floating stage and spring-mounted chassis 301 with inserted cartridge downward onto the pneumatic interface port and heating module as described above.

Docking saddle 400 is bolted on inclined mounting plate 330, and floating stage chassis 301 is suspended on the four-point suspension 600. The suspension springs apply a downward pressure on the floating stage, which is opposed by the suspending action of clamping assembly 800 in the raised position. When clamping the cartridge, clamp gear piece 804 is driven by worm gear 801 and worm gear motor 802, driving travelling axle 803 in a downward arc. The axle pin 803*a* is attached to a cam block (901, visible in FIG. 9B). Linker arm (710, visible in FIGS. 7 and 9A) follows the cam-action of the clamping gear 401 and slider block 901 up or down on the four-point suspension. When disengaging the cartridge, the action is reversed. Worm gear motor 802 is run clockwise, raising pin 803*a* and cam block 901, thus lifting the linker arm 710, which is part of the stage chassis assembly 301, and then reversed (double arrow). When the stage chassis is in the uppermost resting position, the microfluidic cartridge can be removed from the instrument. Mechanical fiducials and alignment pins are used to register the cartridge in the instrument docking bay during the assay.

Figure 8B:
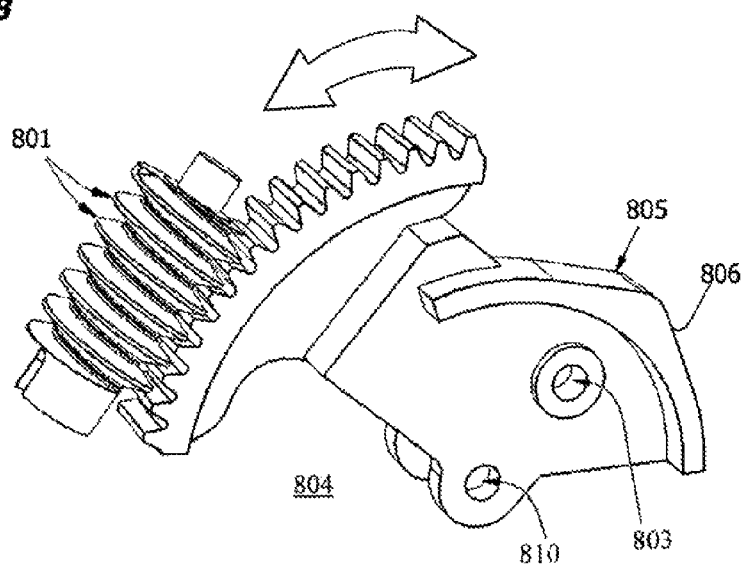

FIG. 8B is a detailed view of the front side of the clamp gear piece 804 and worm drive gear 801, showing also cam follower surfaces 805 and 806 on the anterior edge of the gear member that are used by pressure switches to monitor the position of the gear and actuate coordinated mechanical functions by the host controller. For simplicity, the pressure switches are not shown. Axle 810 is the center of rotation for the piece and rotates on pin 810*a*. Axle 803 travels during rotation of the gear piece, driving a slider block which engages with the stage chassis as shown in the following figure.

Figure 9A:
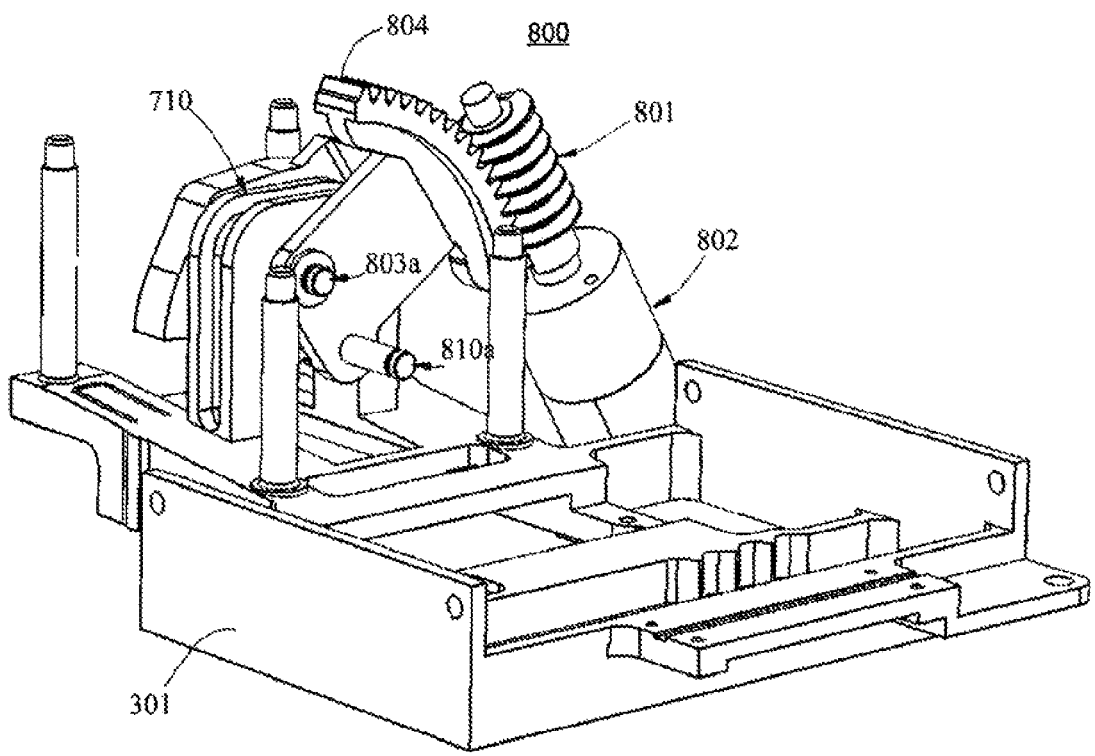
FIGS. 9A and 9B are posterior subassembly views of the clamping mechanism.
Figure 9B:
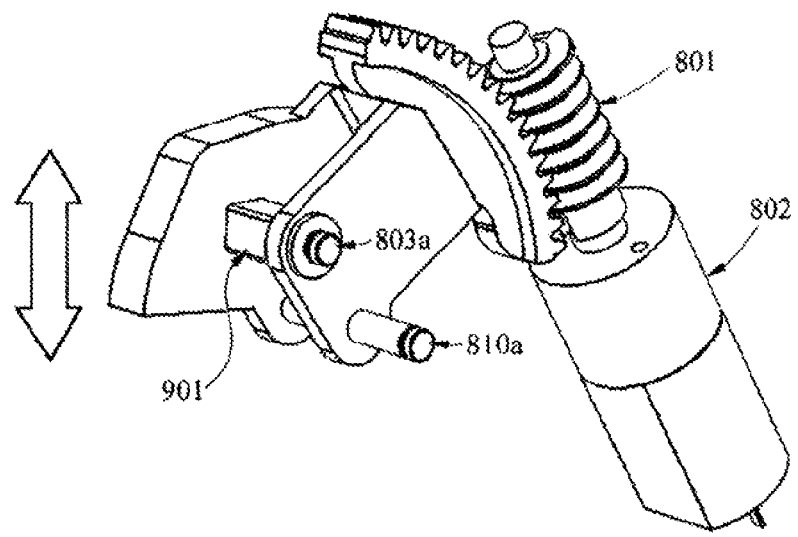

FIG. 9B is a detailed view of the rear side of the clamp gear piece 804 and worm drive gear 801 showing the central axle 810*a* and acentric cam block axle 803*a* and cam slider block (901).

FIGS. 9A and 9B are mechanical drawings showing the action of the clamping mechanism assembly 800. The purpose of the clamp gear-driven cam is to raise and lower the floating stage 301. The clamping gear piece 804 pivots on stationary axle 810, so that travelling axle 803 scribes an arc upward or downward, propelling the linker arm 710 up or down vertically (double arrow). Slider block 901 captive on pin 803*a* slides left to right in a slot 711 in the linker arm (710, see FIG. 7) to accommodate the lateral vector of the motion of the clamp gear while raising or lowering the floating stage 300. The upward movement of the floating stage is opposed by springs 603*a* as shown in the preceding figures.

The mechanism illustrated here is not limiting, insofar as the invention can be realized in alternate ways, for example by clamping up from the bottom rather than down from the top, or by magnetically clamping rather than mechanically clamping. Other spring means may be selected from coil spring, leaf spring, torsion spring, helical spring, and alternatives such as pneumatic canisters (e.g. gas springs) and elastomeric materials or other equivalent means known in the art.

Figure 10:
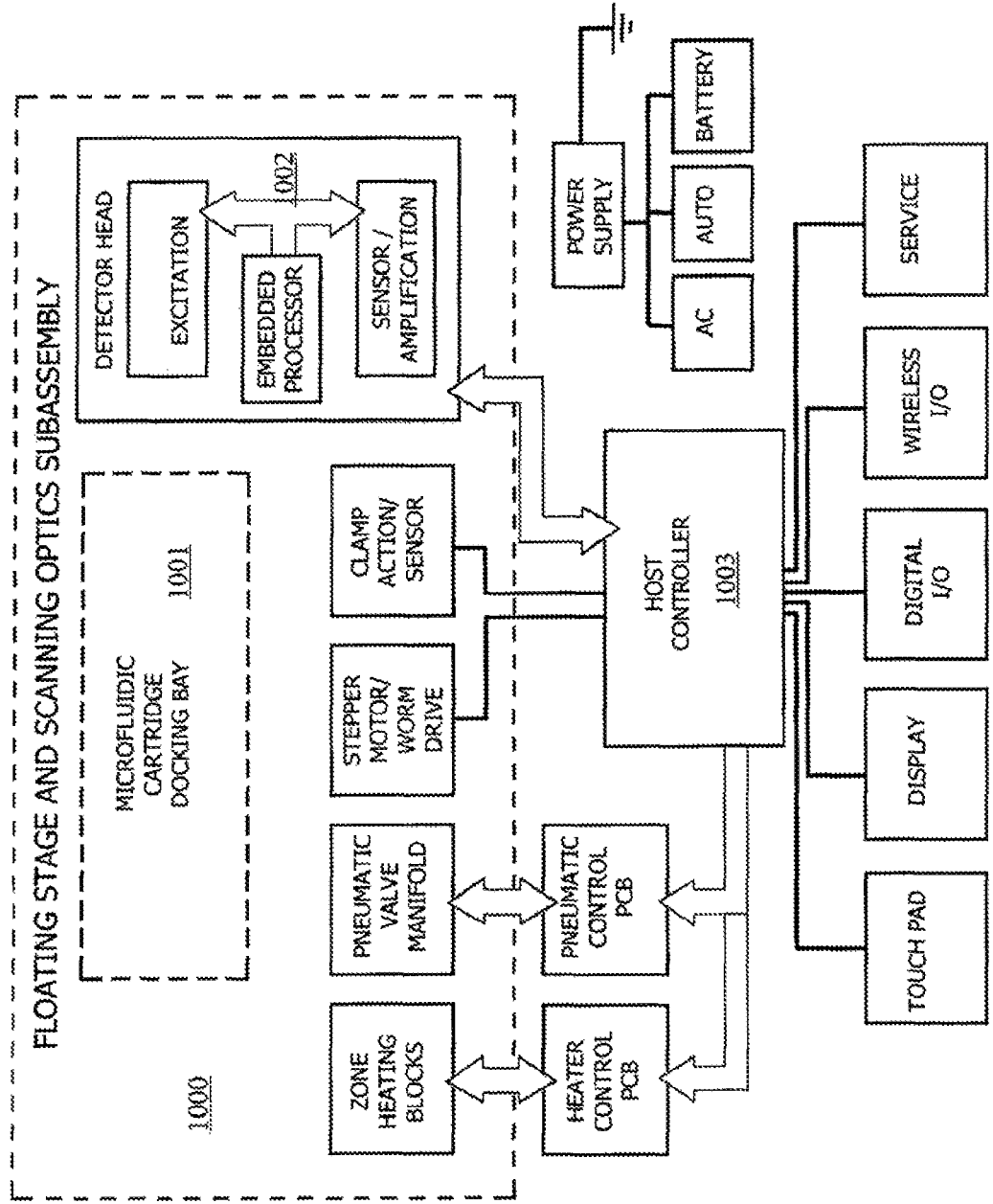
FIG. 10 is a block diagram providing an overview of the functional units, software and firmware of the apparatus.

FIG. 10 is a block diagram providing an overview of the functional units, software and firmware of the apparatus. As described above and presented schematically here, a floating stage (1000, dotted line) within the instrument supports a docking bay 1001 for receiving a microfluidic cartridge and is provided with a scanning detector head 1002. The scanning detector head contains subassemblies for providing excitation light and sensors for detecting, amplifying and processing fluorescent emission signals under control of an embedded microprocessor. Interfacing with the floating stage are a heating module with separately controllable heating zones under control of the host controller, a pneumatics interface connected to pneumatic servos mounted on the base plate 330, which also serves as a pneumatic distribution manifold, a wire harness connecting the stepper motor and the host controller, and wiring harnesses for the clamp motor, and related sensors, including pressure switches for measuring the position of the clamp and the microfluidic cartridge, a barcode reader, and temperature monitors. Optionally, a tilt gauge is also supplied to measure instrument orientation before controls are activated.

Power is supplied to all systems by a rechargeable battery, or by direct connection to an AC converter or to a DC source such as an automobile.

The host controller 1003 is mounted on a motherboard which also contains a touch pad panel for operation of the instrument and an LCD display panel. The instrument may transmit data to an outside network or device via a variety of digital serial I/O links, including a wireless networking card. A special digital junction is provided for service access to the RAM registers and programming, which is software encoded in solid state ROM.

General instructions for operation of the instrument, such as the sequence of pneumatic pulses and valve logic required to operate a particular microfluidic card having the capability to diagnose a particular disease or pathology from a liquid sample, are provided by programmable software in the host instrument. If for example, the barcode reader detects a particular microfluidic cartridge, the device is programmed to perform a particular assay and interpret and display the results in a designated format. However, the operation of the optics, including modulation of source intensity, signal amplification and filtering, is controlled by an embedded microprocessor on the sensor PCB within the detector head. Thus analog operations that are highly sensitive to noise are shielded in the detector head from the more noisy environment of the host instrument, and transmission of analog signals from detector head to host A/D converters is completely avoided. This unconventional separation of functions has happily proved highly advantageous in reducing noise susceptibility of the instrument, as is needed for full portability and field operation.

Figure 11A:
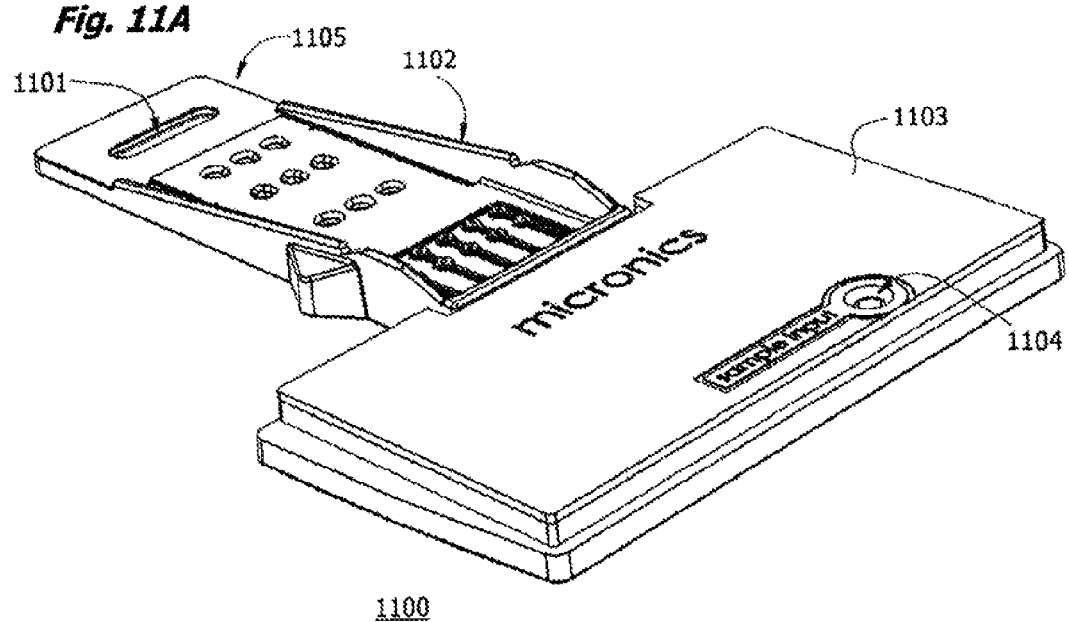
FIGS. 11A and 11B are perspective views of an insertable microfluidic cartridge for use with the apparatus of the invention.
Figure 11B:
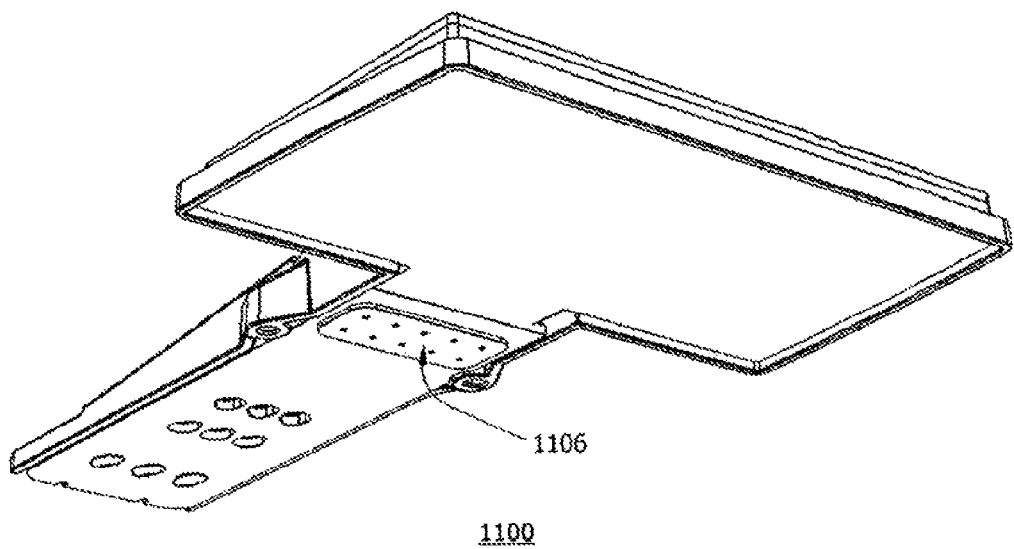
Figure 12:
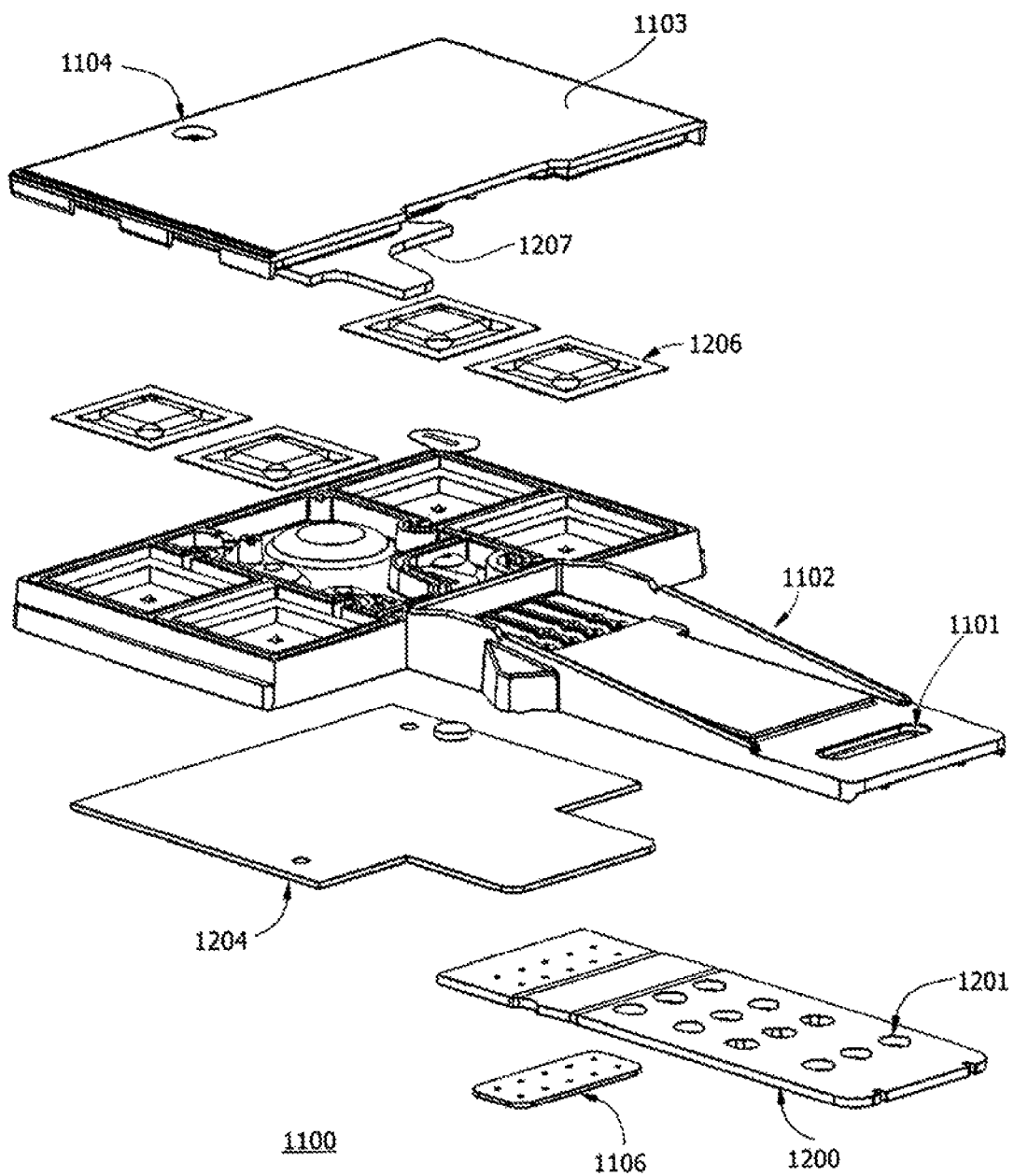
FIG. 12 is an exploded view showing the internal components of a microfluidic cartridge of FIG. 11.

FIGS. 11A and 11B are perspective views of an insertable microfluidic cartridge for use with the apparatus of the invention. The cartridge shown here consists of a housing 1102 and coverplate 1103 with internal workings. Port 1104 is for receiving a liquid sample and anterior nose 1105 is for inserting into the docking bay of the host instrument. Housing cutout 1101 is for exposing optical windows formed in internal subcomponents of the cartridge, as shown in FIG. 12. Gasket 1106 is for sealedly interfacing with the pneumatic interface port 350 of the host instrument.

FIG. 12 is an exploded view showing the internal components of a microfluidic cartridge of FIG. 11. While not limiting in scope by this single embodiment, this particular cartridge 1100 is designed for PCR with FRET or molecular beacon detection. An optical window 1101 on the nose of the housing 1102 inserts into the host instrument and aligns the optical windows of the FRET or molecular beacon detection chambers 1201 of the microfluidic inboard circuit card 1200 with the optical path scanned by the detector head. Added microfluidic processing related to sample preparation is supplied on outboard card 1204. All liquid reagents are enclosed in sealed frangible pouches 1206 and are dispensed when needed under pneumatic control. Other reagents are provided on-card in dry form. Fluid waste is sequestered in an adsorbent batting 1207 that is sealed in place under the plastic coverplate 1103. The details are beyond the present scope, but microfluidic circuit 1200 with internal microfluidic channels and wells for thermocycling and amplifying a nucleic acid target includes detection chambers 1201 for FRET detection of any resultant amplicon. The cartridge as shown is a disposable cartridge. Gasket material 1106 serves as a single-use sealing gasket between pneumatic control ports on the microfluidic cartridge and a corresponding pneumatic control manifold and interface 350 on the inclined mounting plate 330.

Figure 13:
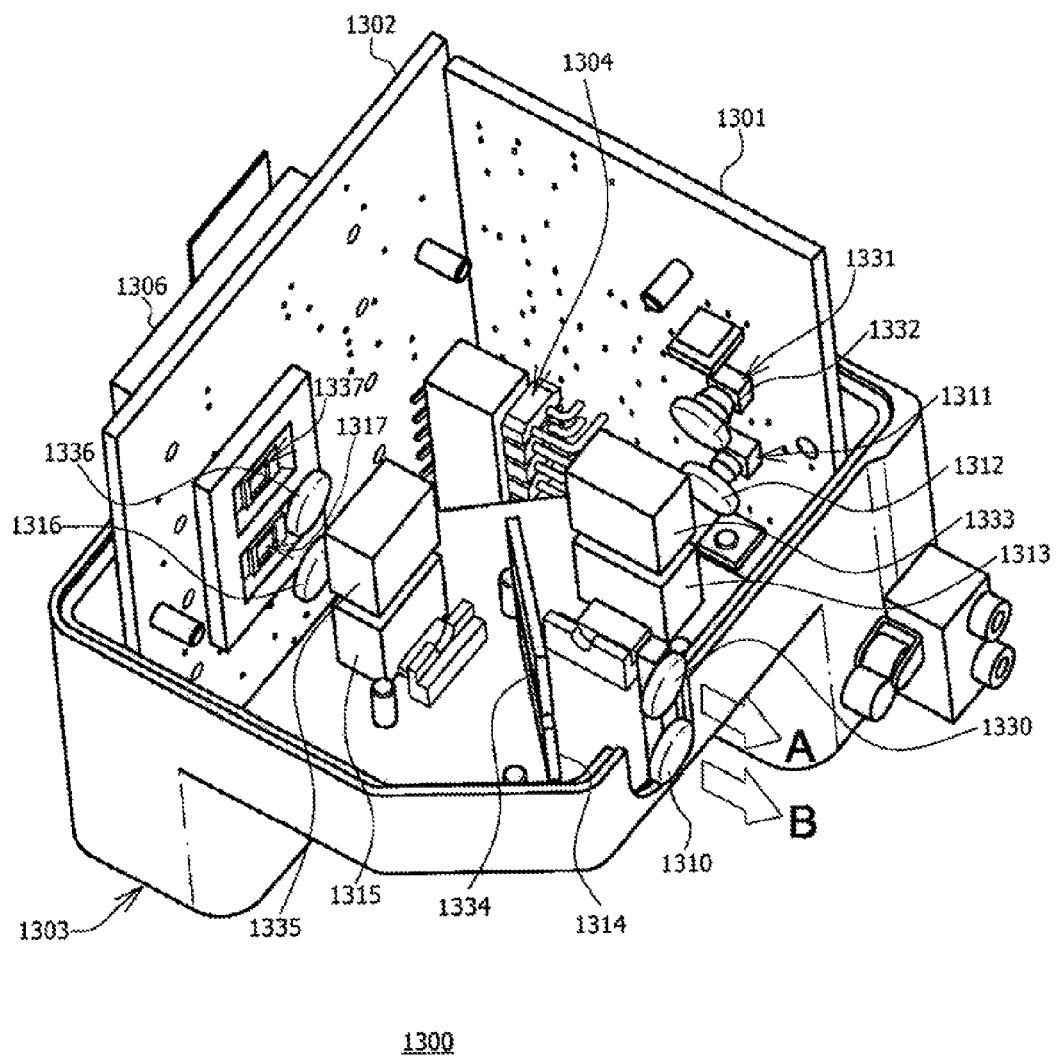
FIG. 13 is a perspective view of a detector head with dual optical channels and electronically isolated circuit boards for excitation and emissions detection. One half of the housing is removed in order to view the internal components.

FIG. 13 is a perspective view of a dual channel detector head 1300 with two optical channels and electronically isolated circuit boards (1301,1302) for excitation and for emissions detection respectively. In this view, the upper half of the housing 1303 is removed in order to show the internal components of the detector head. The dual channels are marked by objective lenses (1310, 1330) and optic pathways A and B (open arrows). The SMD LED excitation light sources (1311, 1331) are mounted on a source LED printed circuit board (1301), which is connected at right angles to sensor PCB (1302) via an edge-type resistive pin-connector (1304). The photodetection components are mounted on the sensor PCB (1302). A Faraday cage element (1306) is used to shield the photodiodes (1317) and (1337) and surrounding high gain amplification circuitry.

Fluorescent excitation is provided in the target channel (Arrow A) by a surface mounted LED (1331) which is chosen to match the excitation spectrum of the target fluorophore. Source LED (1331) emits a divergent light beam, and the radiated light beam is then collimated by source excitation lens (1332). Source lens (1332) is a planoconvex lens having its flat surface facing the LED. The collimated light beam may then be passed through an excitation bandpass filter (1333), the purpose of which is further explained in the description associated with FIG. 20. The collimated, filtered excitation light beam is then reflected from a dichroic mirror element or beamsplitter (1334), which is installed at a forty-five degree angle to the incident beam, and is passed through a planoconvex objective lens (1330) and through an external window in the detector housing (Arrow A). After passing lens 1330, the excitation light is focused through a detection chamber (not shown, see FIGS. 14-17) embedded in a microfluidic cartridge, which contains a sample liquid with any target fluorophore. The path length of the excitation light through the sample liquid is doubled by use of a back mirror behind the microfluidic cartridge. The target fluorophore is excited by the incident light beam. The emission of the fluorophore is generally at a longer wavelength than the excitation wavelength and is shifted by an amount equal to the Stokes shift of the target fluorophore.

A portion of the returning emission from the target fluorophore in the detection chamber is collected by planoconvex sampling lens 1330 and is collimated before striking dichroic mirror 1334. Optionally, a Fresnel lens may be use to further reduce the working distance between the lens and the sample so as to optimize collection of emitted light, which is further enhanced by back mirror mounted on a heating block behind the detection chamber. Because dichroic beamsplitter 1334 has a wavelength cutoff between the excitation and emission wavelength, the dichroic mirror 1334 now acts as a pass-band beam splitter for the emitted fluorescent light beam and a stopband filter for the excitation light. It transmits the emitted fluorescent light while reflecting reflected excitation light and any ambient light entering the light path through the objective lens window. Emitted light passing through the dichroic beamsplitter 1334 then passes through an emission filter 1335, the purpose of which is further explained in the description associated with FIG. 20. Light exiting emission filter 1335 then passes through planoconvex sensor lens 1336, where it is focused onto the surface of a photo-sensor 1337 which is surface mounted to PCB 1302 and is protected from electrical noise by Faraday cage 1306.

The above described optical pathways are repeated in a second (control) channel having control excitation LED 1311, planoconvex excitation lens 1312, excitation filter 1313, dichroic beamsplitter 1314, objective lens 1310, control emission filter 1315, planoconvex sensor lens 1316, and control photodiode 1317. Outputs from both photodiodes are amplified by three-stage trans-impedance amplifiers built into the board next to the photodiodes and grounded to an embedded microprocessor on the sensor PCB via carefully shielded pins from the amplifiers.

In one embodiment, as exemplified by the use of fluorescein and Texas Red as fluorophores, excitation LED 1331 is a 470 nm LED with band-pass excitation filter 1333 for delivering essentially monochromatic light of 485±12 nm used for the target channel and a 590 nm LED 1311 with band pass filter 1313 was used for the control channel. The excitation LEDs are modulated or "strobed" on and off using a strobe rate of 130 Hz so as to filter AC power-related noise at 50 or 60 Hz and at harmonic frequencies associated with fluorescent overhead illumination, also filtering phantom signal related to stray ambient light and electrical noise that may be present at 30 or 60 Hz. Local feedback sensors are used to monitor and stabilize source LED output intensity. Detection monitoring of fluorophore emission is coordinated with movement on rails of the detector head under power of a stepper motor controlled by a host controller. An embedded microprocessor and associated circuitry in the detector head is provided with RAM memory, ROM memory, an A-D converter, a three-stage trans-impedance amplifier, and signal processing and command sequence firmware to handle these functions.

Each of the photo-sensors 1317 and 1337 are mounted on a common PCB 1302. The output signal legs from each of these photo-sensors are connected directly to the first stage of respective tri-stage trans-impedance amplifiers (not shown). PCB 1302 makes extensive use of hardware noise-reduction components, in particular an embedded ground plane and a Faraday Cage 1306 to minimize the unwanted effects of any RF or electromagnetic interference on the input signals. The combination of the use of these hardware noise-reduction elements with a digital signal processing (DSP) method, leads to a detector design which is essentially immune from the effects of unwanted noise.

Figure 14A:
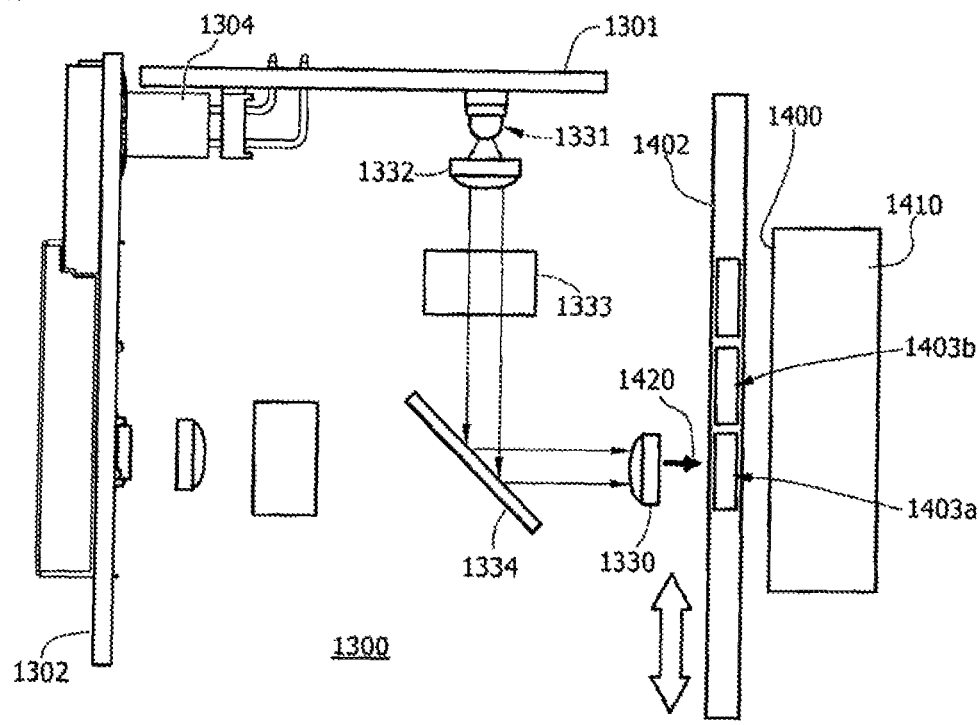
FIGS. 14A and 14B are schematic views of the internal optical components of a fluorescence detector with dual optical channels, heating block-mounted mirror and microfluidic cartridge. Excitation optics are mounted on one circuit board and detection optics on another to reduce noise interference.
Figure 14B:
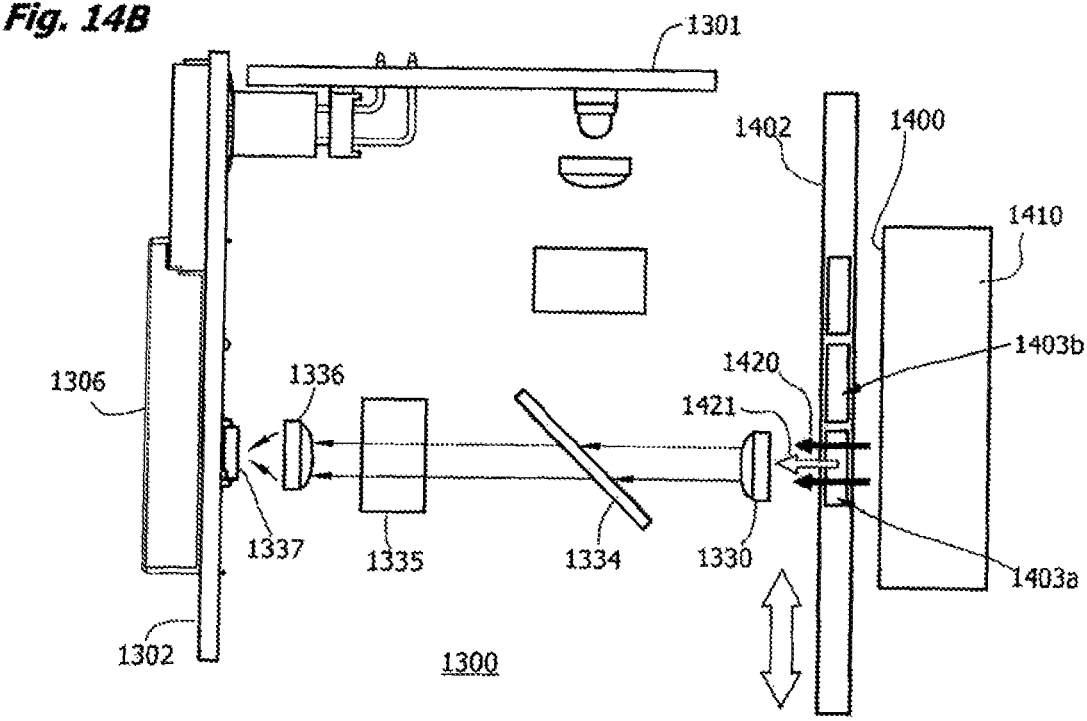

FIGS. 14A and 14B are schematic views of the internal optical components of a fluorescence detector head 1300, showing the external optical interface with optical windows in a microfluidic cartridge 1402 and back mirror 1400 mounted behind the cartridge on the surface of a heating block 1410 that is used to control or ramp the temperature in detection chambers enclosed in the cartridge. Unconventionally, multiple independent optic pathways or "channels" are formed in a single detection head and share electronic PCBs and downstream signal processing circuitry, but excitation optics are mounted on one circuit board and detection optics on another to reduce noise interference. The two boards are electrically coupled by a corner mounted pin junction 1304 and are electronically isolated.

Shown in FIG. 14A is the optical transition for the excitation of a fluorophore in a detection well (1403a or 1403b) embedded within a microfluidic cartridge 1402. The head is a scanning head and moves across microfluidic cartridge 1402 (double arrow). Light from excitation LED 1331 on PCB 1301 is collimated by lens 1332 and made essentially monochromatic by band-pass filter 1333. Any fluorophore or fluorophores in detection well 1403a (whether the control or the target fluorophore) are excited by incident light 1420 focused on the sample by objective lens 1330. In FIG. 14B, the emission of the fluorophore(s) is collected by objective lens 1330 and transmitted to sensor 1337 after passing through dichroic beamsplitter 1334, emission filter 1335 and sensor lens 1336. Sensor 1337 is in direct electrical contact with the base of a high gain transistor that amplifies the output signal and is shielded in a Faraday cage 1306. The emitted fluorescent light is generally at a longer wavelength according to the Stokes shift of the fluorophore, enabling the emitted light to pass through dichroic bandpass mirror 1334 and emission bandpass filter 1335 without losses. Mirror face 1400 is used to increase the amount of excitation light on the target, doubling the excitation path length, and to improve emission collection efficiency. The light returned from sample chamber 1403a to objective lens 1330 is thus a mixture of emitted and reflected fluorescence 1421 and reflected excitation light 1420. Light traps (not shown) are provided to capture stray reflections. Reflected light 1420 does not pass dichroic mirror 1334 and is returned to the source, and does not interfere with the measurement of emission intensity at sensor 1337. The optic elements of a single channel, including excitation source, source collimating lens, excitation filter, dichroic mirror, objective lens, excitation filter, sensor lens, and detector with amplifier make up an optics module having an essentially monochromatic source wavelength and a highly specific sensor for detecting fluorescence at a particular wavelength characteristic of the target (or control) fluorophore. One optics module or channel may be used for an assay target, the other module for a control channel. Tandem mounted optics channels may be used to collect data on a plurality of fluorophores, where electrical processing is shared by common embedded microprocessor before transmission to the host instrument. Optionally additional channels may be use. Each channel shares the two PCB but has separate optics.

The microfluidic cartridge 1402 is movable (double arrow) relative to detector head 1300 and motorization of the detector head or cartridge tray or mounting chassis permits scanning: a transect across cartridge 1402 permits measurements to be made on sample chambers 1403a and 1403b, for example. By using multiple detection optics modules mounted side-by-side in a detector head, the sample chambers can be scanned for multiple fluorophores in series.

According to one embodiment, the excitation electronics are mounted on a printed circuit board (1301) and the detection electronics are mounted on a second PCB (1302). An edge-connector 1304 electrically joins the boards. Faraday cage 1306 protects the sensor and associated high gain amplifier from stray electromagnetic noise. Mirror 1400 is fabricated on the upper surface of heating block 1410, which also functions in heat transfer and controls the temperature of the sample fluid during the assay. The temperature of heating block 1410 can be ramped, for example as in a FRET melt determination under control of the host controller.

Figure 15:
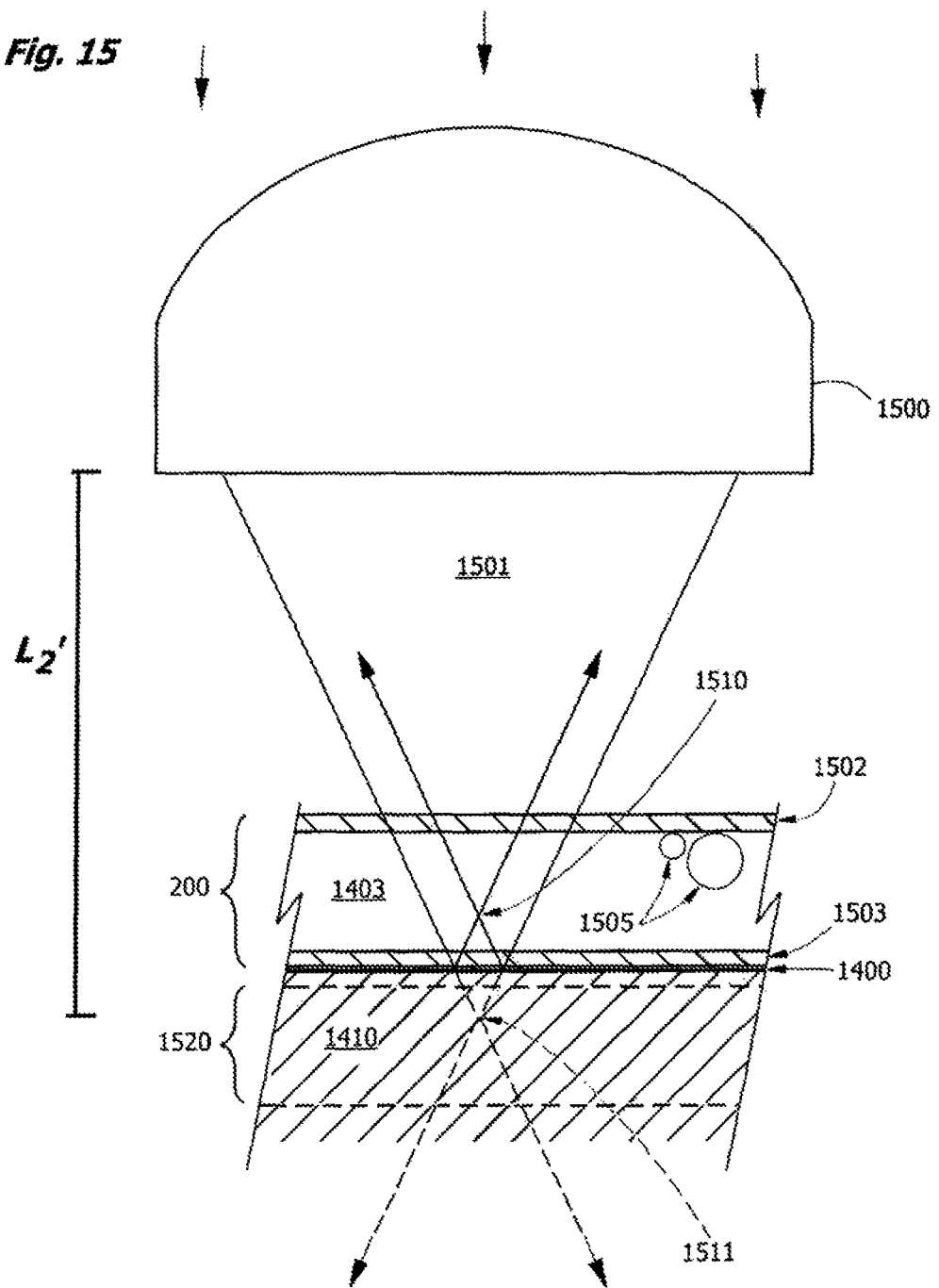
FIG. 15 is a representation of an excitation cone and planoconvex objective lens relative to the cartridge detection chamber and mirror-faced heating block.

FIG. 15 is a representation of a planoconvex objective lens 1500 and excitation cone 1501 relative to the cartridge detection chamber 1403 and heating block 1410 with mirror face 1400. The excitation cone is formed by diverging rays illuminating the lens so that the distance L2' is greater than the native focal length L2 of the lens. By convention, the native back focal length L2 of the lens is determined using collimated light. Shifting the focal position is termed "decoupling".

Interposed between the lens 1500 and the mirror face 1400 is a microfluidic cartridge 200 with detection chamber 1403. The detection chamber is bounded by an upper optical window 1502 and a lower thermo-optical window 1503. In operation, the intervening volume is taken up by a liquid sample, shown here with two entrained bubbles 1505. The focal cone is seen to reflect from the mirror face, forming a real image (1510, solid rays) of the source in the detection chamber and a virtual image (1511, dotted rays) of the source below the mirror face. The back focal position L2' is thus generally equal to or greater than the distance between the lens and the mirror. Excitation light striking the mirror is reflected as a focused beam in the fluid volume of the detection chamber, thus doubling the length of the light path of the excitation light through the sample and increasing the excitation fluorescence yield. The back focal position L2' is not equal to the back focal length L2 of lens 1500; the two are decoupled, generally by illuminating the lens with a divergent beam from the source.

Figure 16:
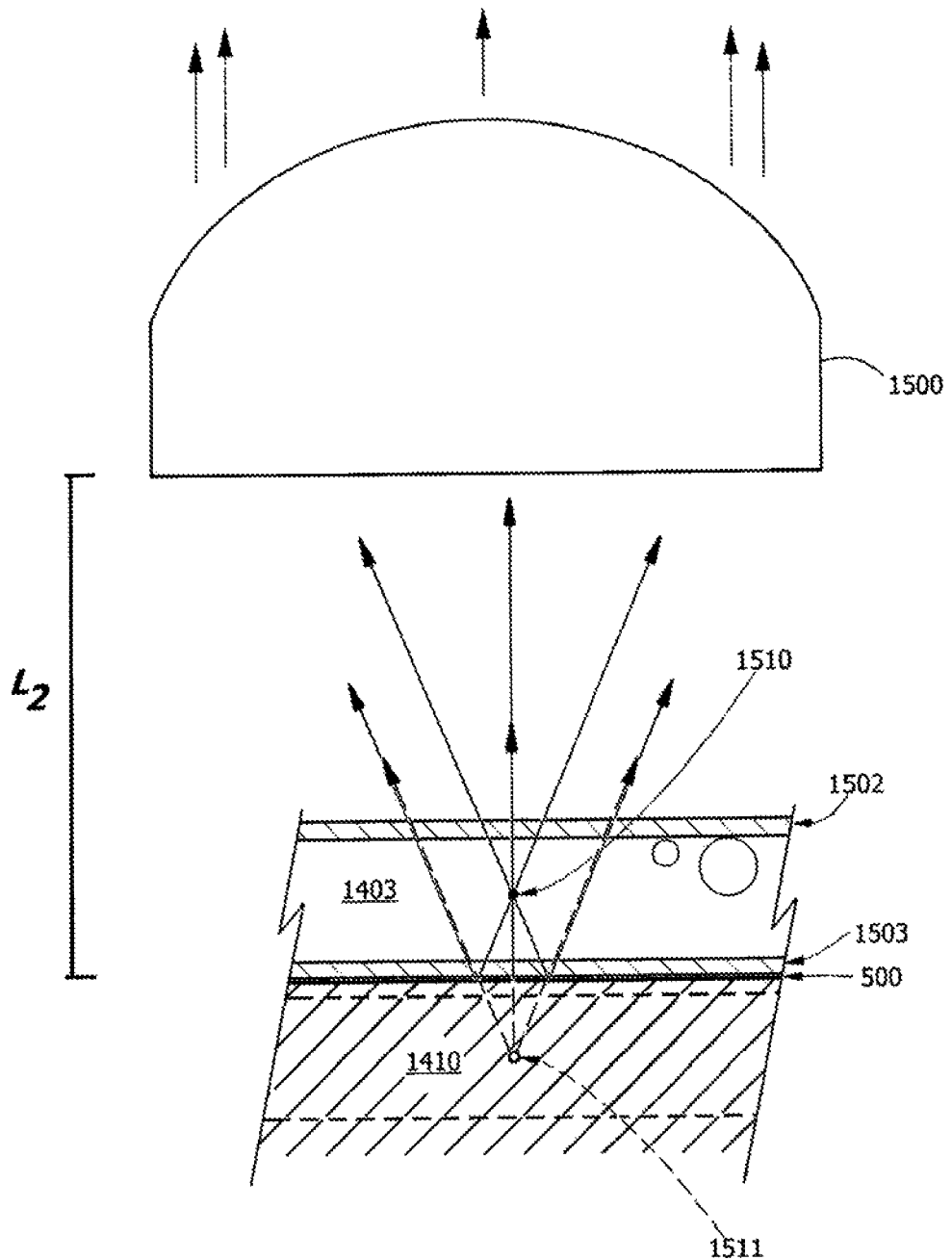
FIG. 16 is a representation of emission collection with a planoconvex objective lens at short working distance relative to the cartridge detection chamber and mirror-faced heating block. Shown are primary and reflected fluorescent emissions.

FIG. 16 is a representation of the objective lens of FIG. 15 in emission collection mode. Shown are primary and reflected fluorescent emissions (solid and dotted lines from a real image 1510 and a virtual image 1511). Again shown are bubbles in the chamber 1403. Rays striking the planar back surface of the lens will be collimated and transmitted to a detector. The quantity of fluorescence signal captured depends on the angular and numerical apertures of the objective lens 1500. The native back focal length of the lens 1500 is L2. The back focal length and back focal position of the lens (L2 versus L2') can be manipulated or "decoupled" by repositioning the source as shown below.

Figure 17:
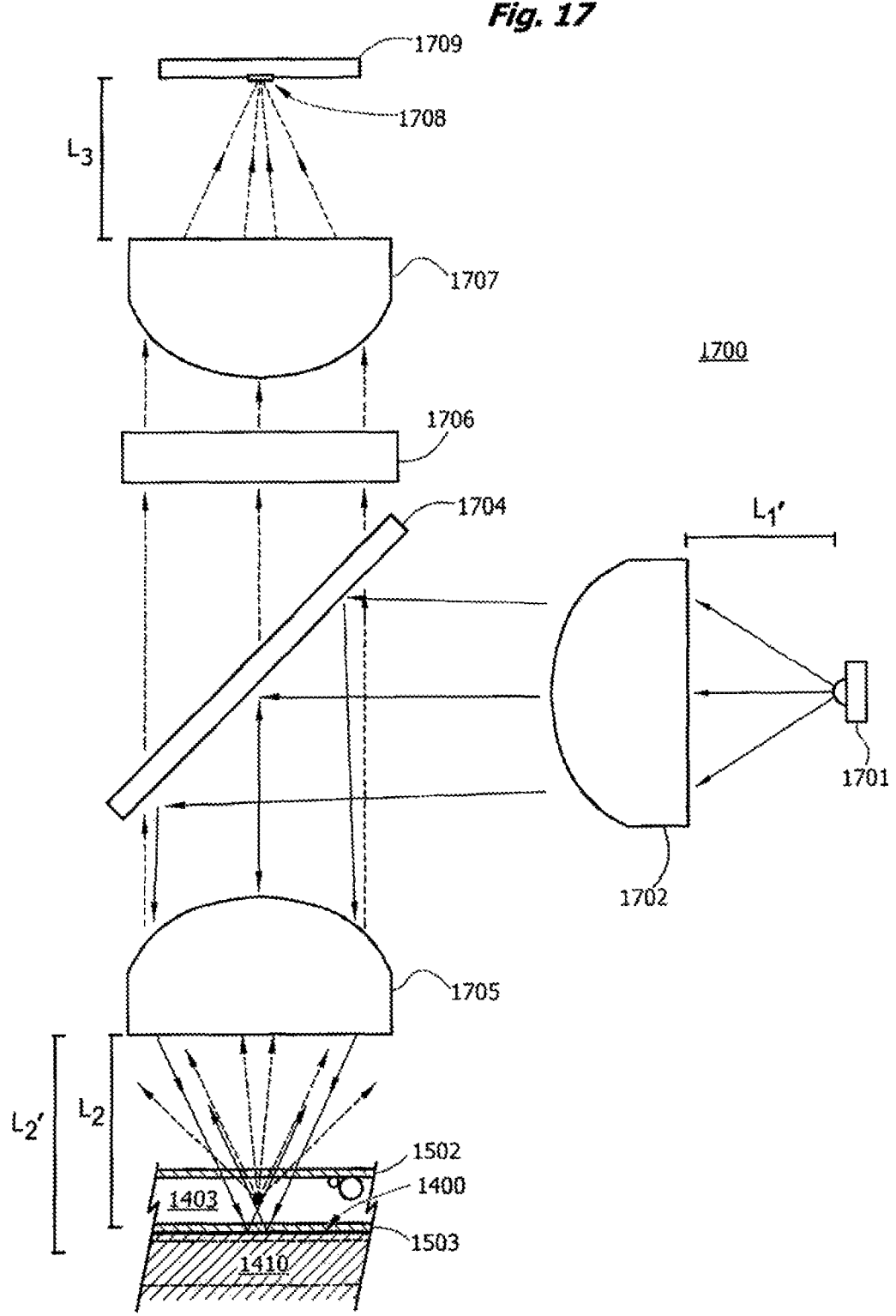
FIG. 17 is a schematic representation of an optical pathway with decoupled excitation and emission optics.

FIG. 17 is a schematic representation of an optical pathway 1700 with decoupled excitation and emission optics. In this figure, excitation rays are shown as solid lines and emission rays are shown as dotted lines. Aspects of integration of the emission and detection elements into an integrated optical system are discussed. Here the light source 1701, may be an LED as shown, an SMD LED without lens housing and reflector ring, an SLED, a pumping laser diode, a ridge-waveguide (Fabry Perot) laser diode, a tunable laser, and so forth, such source of illumination preferably having a narrow bandwidth and serving as a directed source of collimated light. LEDs of various narrow bandwidths are available, for example with peak emission at 630 nm (red), 470 nm (blue), 525 nm (green), 601 nm (orange), 588 nm (yellow) and so forth. While LEDs may also be used if desired, but generally the LED output is matched with the fluorophore of the target in the assay and an optional excitation filter (not shown) may be used to sharpen the bandpass as required. Light output of light source 1701 is transmitted by source lens 1702, shown here as a planoconvex lens, although molded asphere may also be used, and optionally passed through a excitation filter (not shown) before striking dichroic mirror element 1704, where the excitation beam is redirected to objective lens 1705. The excitation cone striking sample fluid volume 1720 in microfluidic cartridge 1402 is shown with solid lines. Unconventionally, the focal point of the excitation cone has been projected past the sample chamber and back mirror 1400 by moving the source 1701 closer to the source lens 1702 (ie. shortening distance L1' in order to increase distance L2', where distance L1 would be the native back focal length of lens 1702). As distance L1' is shortened, the source rays striking the objective lens are caused to diverge, thus increasing distance L2'. The native back focal length of objective lens 1705 is L2 and emissions from a fluorophore in the sample chamber and reflected rays from the mirror are collected as a virtual image of the fluorophore that enter the objective lens in a cone having a focal point decoupled from the focal point of the excitation light (which is focused behind the mirror). The reflected virtual image of a population of fluorophores in the chamber is bounded by dotted lines crossing the heating block 1410. Fluorescent emissions within the focal length L2 are effectively collimated by the objective lens; are transmitted through dichroic mirror 1704, bandpass filter 1706, and are then focused by sensor lens 1707 onto sensor 1708, which is generally mounted on a PCB or other solid support 1709. Lens 1707 has a back focal length L3 that generally is equal to back focal length L2 of objective lens 1705. However, a larger lens 1707 may be used to better utilize the surface area of the sensor 1707, which is for example a photodiode or CCD chip. Optimization of signal may require independent adjustment of each lens according to these principles.

The excitation light emerging from objective lens 1705 and the emission light entering objective lens 1705 are operably decoupled in different focal cones (L2' versus L2 respectively). A distance separates the actual focal plane of the excitation light and the native focal length of the objective lens, which can capture light in a broad plane of origin of the fluorescent emissions when excited using a mirror and an extended focal position of the excitation cone 1501. This phenomenon, termed "decoupling" was found to increase capture of fluorescent emissions when a back mirror is used, and controverts earlier teachings in favor of the confocal approach of the prior art.

While the teachings of the prior art strongly support making the excitation and emission confocal, there is in fact an hithertofor unseen advantage in decoupling the focus of the source from the emission cone and using a back mirror 1400. Emitted light arises from a greater area and depth throughout the sample cartridge, thus overcoming any lack of signal from dead spots or inhomogeneities as would be due to small bubbles, unmixed areas, or quenched probe. Greater reliability is achieved at the expense of some selectivity in the excitation at the point of focus. This is a technological advance in the art.

To summarize, generally, L2' may be greater than L2 and L3. L1 advantageously may be configured so that the cone of excitation light falls behind the sample chamber 1403 and most preferentially close to or behind the back mirror 1400. In a preferred embodiment, the focal point of the excitation cone falls on or behind the back mirror. The objective lens is configured, generally, so that emitted light is efficiently collected and collimated for projection onto the detection sensor by a symmetrical cone of emitted light from sensor lens 1707 (i.e. L2=L3).

Accordingly, in another embodiment the apparatus of the invention employs lenses configured so that excitation optics and the emission optics are decoupled. In a first embodiment of this apparatus, the light source is positioned at a distance L1' from the source lens, where L1'<L1, whereby the excitation optics and emission optics are decoupled by transitioning the excitation cone to a focal position L2' at or behind the mirror face, such that L2'>L2. In a second embodiment, the source lens is configured to form a diverging beam of light incident on the objective lens, thereby positioning the excitation cone at a focal position L2', whereby L2'>L2.

Advantageously, L2 is configured to be symmetrical to L3 (i.e., L2=L3), so that the operation of detector 1708 is optimized and robust. The sensor photodiode is preferentially configured to be large enough with reference to the cone of focus of lenses 1705 and 1707 to accommodate some degree of misalignment without loss of assay validity.

Performance is improved not only in assays where differentiation of a positive or negative assay result is required, but also in assays were some level of quantitation is required, as for example schizont or merozoite copy number in the case of *Plasmodium falciparum*. It should be recalled that the original purpose of confocal optics, as articulated by its inventor, Minsky in 1957 (U.S. Pat. No. 3,013,467), was to create a three-dimension image of a thick solid specimen by rastoring a focal point of excitation across and through the specimen (xyz axis rastoring) while monitoring emission only from the area of the specimen where the excitation cone is focused at any given time. In contrast, in a fluid mixing specimen that is generally homogeneous, an opposite effect is desired, that of measuring the cumulative fluorescence of the entire specimen, and suppressing any localized variance in that fluorescence. Thus by reformulating the problem, we have been able to design a novel optical system with back mirror, with decoupling of the focal plane of excitation and emission, with the happy result that fluorescence detection is more sensitive and robust in the presence of occasional optical interferences.

Figure 18:
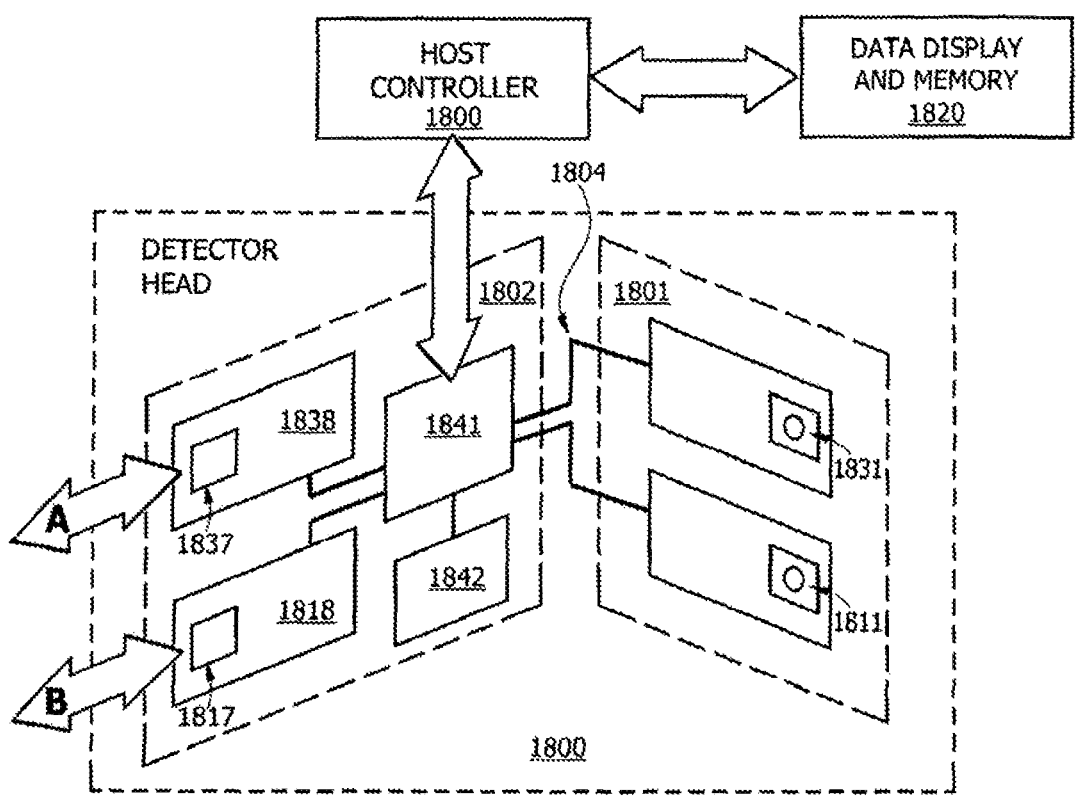
FIG. 18 is a block diagram of the detector head electronics used for controlling the fluorescent excitation, and receiving, processing, and digitally communicating fluorescence emission signals to the host instrument.

FIG. 18 is a block diagram of the detector head electronics and optics used for controlling the fluorescent excitation and for receiving, processing, and digitally communicating fluorescence emission signals to the host instrument. Optical channels are again identified by open arrows A and B. Channel A is taken as a control channel and channel B as a target analyte channel, but the roles are interchangeable. The electronic functional blocks in each channel, source excitation circuits (1811,1831) and sensor circuits (1817,1837) are identical and are driven by detection optics control circuitry of the embedded microprocessor 1841, which has a dedicated on-board instruction set as firmware, typically as a socketed EEPROM chip 1842. The circuit board 1801 for the source LEDs can support multiple LEDs, and the circuit board 1802 for the sensor circuit can support multiple photodiodes. Each photodiode is intimately associated with a multiple stage high gain amplifier (1818,1838) and the two circuit boards are electronically isolated with separate grounds.

The stepper motor and worm drive module controls scanning of the detector head as directed by the host controller. Thus the detector head operates as a self-contained optics and signal analysis module while scanning under control of the host controller. The host also handles the data tabulation and display functional block (1820), including preparation of test result reports and any I/O functions.

Within the detector head, each of the LEDs associated with source excitation circuits (1811, 1831) are modulated by a square wave at a frequency of 130 Hz. The reason for this modulation is related to noise reduction measures from the following potential noise sources:
1. 50/60 Hz mains
2. 100/120 Hz second mains harmonic from the fluorescent lights.
3. Third and higher harmonics of 50/60 Hz.
4. Differential frequencies (rumble) of 130 Hz and all the above of the
5. Photodiode sensor, first stage feedback resistor and amplifier electrical noise. This noise is wide band white noise.

In order to retrieve the useful signal from the noisy source, the following methods are employed:
1. Fast sampling and averaging of taken data in order to avoid aliasing and at the same time limit noise bandwidth.
2. Modulation of the LED light at 130 Hz and correlation with the detected fluorescence signal at 130 Hz in order to reject all uncorrelated components. The 130 Hz modulating frequency was selected to provide at least 10 Hz difference from the 50/60 Hz mains and its harmonics (mainly 100, 120, 150 and 180 Hz).
3. Further filtering and processing of the correlated data to eliminate electromagnetic noise from mains power supplies of either 50 Hz or 60 Hz or harmonics thereof.

The advantage of using the embedded microprocessor 1841 with the fluorescence detector is that a proprietary method of digital signal processing (DSP) may be programmed into the firmware of an embedded microprocessor in the detector to eliminate noise before transferring a digitized signal to the host controller.

The excitation LEDs are modulated at 130 Hz with 100% AM modulation depth (on/off). The modulating frequency was selected to provide sufficient separation from 50/60 z and its harmonics (50, 60, 100, 120, 150, 180 Hz, et seq.). Any intermodulation product frequency is at least 10 Hz and can be filtered out during signal processing. The LEDs are driven by FAN5612 LED-drivers (LED drivers available from Fairchild Semiconductor®). Each driver is capable of sinking current up to 120 mA (40 mA on each of three outputs) at the required frequency.

The host controller 1800 is responsible for the operator interface, including display of results, and for operation of mechanical and pneumatic functions required to perform an on-cartridge assay and detector head scan. The embedded microprocessor 1841 in the detector head is responsible for controlling the excitation and detection circuits, which are electronically isolated on separate PCB boards (1801,1802) and for signal filtering, and has its own instruction set which is programmable as a socketed EEPROM chip 1842 on the sensor board. The clock frequency of the embedded detector head microprocessor is used to strobe the excitation LEDs and to synchronize pulse collection in the sensor diodes. A separate clock in the host controller is used to drive the stepper motor during scanning. Multiple excitation and detection optics can be housed in a single detector head so that signal excitation and fluorescent emission detection can be multiplexed in the embedded processor. We have found that on-board packaging of signal processing achieves a low noise environment with improved signal-to-noise ratio and sensitivity by minimizing signal pathlengths and permitting effective use of faraday shielding where necessary, such as around the sensor diode leads and at the junction between the excitation and sensor circuit boards.

Isolation of dual channels proved an advantageous means to implement multiplex assays where target fluorophore and internal control fluorophore are mixed in a common liquid sample. By separating target and control channel optics, crosstalk that could lead to false positive tests or test rejection due to invalid control results was eliminated.

The host controller also controls pneumatic valve logic and pulse trains for operating diaphragm pumps in the microfluidic cartridge during the assay, any resistive or Peltier-type heating elements associated with thermal cycling of the sample, and optionally may perform melt curves in the detection chamber. Other optional components include fiducials for aligning detector heads and a bar code reader for sensing information printed on the insertable microfluidic cartridges.

The host controller program with program coding means is designed to perform all the steps of a fluorescence assay process and to transform and format a signal or other data from the fluorescence detector into a machine-readable or graphical report of significance to the user. The program can be integrated into the fluorescence detector instrument as shown here or can be connected to it through data lines or wireless interfaces as part of a network, intranet or internet. Generally, a serial asynchronous communications interface is provided for communication with the host controller on the instrument motherboard or on an external network.

Similarly, results, data, error codes, status updates, and so forth can be sent via common electronic interfaces and data lines such as USB (Universal Serial Bus), RS232 (Recommended Standard 232, a serial port connector) or FireWire® (serial bus) and via a wireless transmission system such as IR-transmission, Bluetooth® wireless technology for exchanging data over short distances), GSM (Global System for Mobil Communications), GPRS (General Packet Radio Service), RSID (Remote Subscriber Identification:), etc. Programming, reprogramming, calibration, and recalibration as well as system diagnosis of the device is possible via common electronic interfaces and data lines such as USB, RS232 or FireWire® and via a wireless transmission system such as IR-transmission, Bluetooth®, GSM, GPRS, RSID, etc.

The apparatus can be configured for wavelengths in the UV, visible region, and near infrared spectrum. For applications in fluorescence mode, which is one of the preferred operating modes, the device can be configured for specific fluorescence dyes with excitation spectrum in the UV and visible spectrum and for emission in the UV, visible and near infrared spectrum. While a red shift is more typical, up-converting fluorophores may also be used. Today available light sources filters and available dyes allow for customizing in the range of 300 to 900 nm.

Figure 19A:
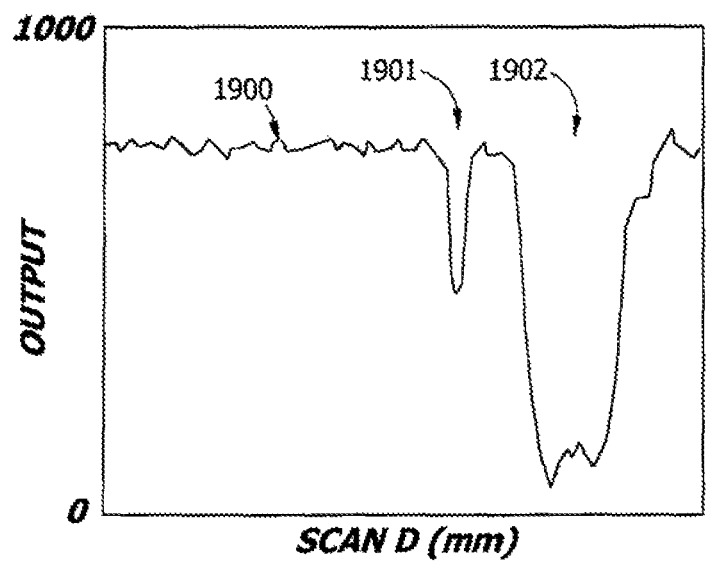
FIGS. 19A and 19B are representations of raw input and digitized output showing digital removal of bubble interference.
Figure 19B:
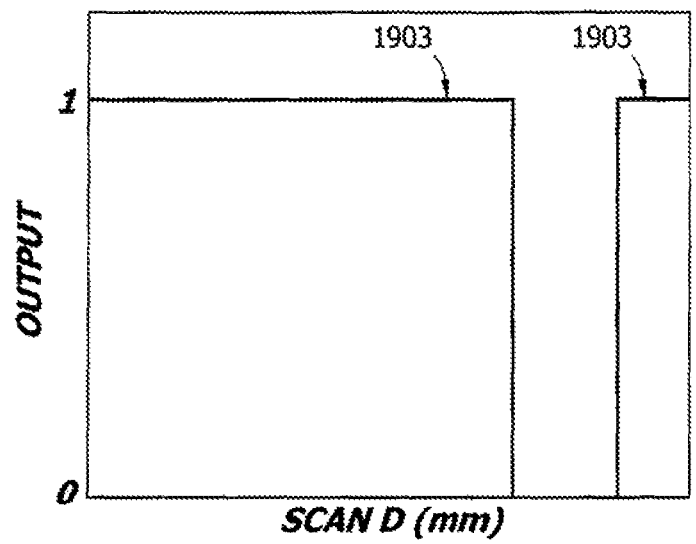

FIGS. 19A and 19B are representations of raw input and digitized output showing digital removal of bubble interference. In FIG. 19A, output (1900) from the photodiode after amplification is represented. The level of noise is generally low, but signal deteriorates at 1901 and 1902 due to the presence of two small bubbles in the detection chamber (see FIG. 15), for illustration. The processor applies a threshold to the output signal and scores the signal "high" (i.e. a one) if the signal is above the threshold and "low" (i.e. a zero) if the signal is below the threshold. Since no signal output can be above the threshold except in the presence of a fluorophore matched to the emission optics and filters, any positive signal (1903) is a positive assay for the presence of fluorophore. The threshold comparator can be adjusted based on experience with clinical samples in the assay. Thus a "1-bit" digital transformation of the scanning image data removes any interference from bubbles. We have found surprisingly that when a fluorophore is present but multiple bubbles fill the chamber, light refracted around or through the bubbles will result in a positive signal. The system is thus very error resistant and robust for qualitative testing, such as is needed in diagnostic assays for infectious disease. The signal comparator is a digital function of the microprocessor and firmware embedded in the detector head and is independent of host controller function.

Should the presence of a positive fluorescence signal indicate a negative assay result, the system can be easily configured to score the test that way. Thus the use of a 1-bit digital transformation is a remarkably simple and effective solution for the presence of bubbles in a microfluidic assay. Because of the nature of the mixing and heating operations in microfluidic assays, and the frequent use of surfactants, the presence of bubbles is not uncommon. The systems described here use a combination of physical methods (venting, tilting of the stage, wetout under low dead volume conditions, accentric channels between mixing chambers) and signal processing methods to achieve robust assay performance such as is needed for reliable operation outside the controlled environment of a clinical laboratory.

FIGS. 20A and 20B show the excitation and emission spectra of a typical system of mixed fluorophores for the target and control, here illustrated by fluorescein and Texas Red. Shown in FIG. 20A, curve 2001 is the excitation spectrum for fluorescein (dotted line); curve 2002 is the emission spectrum (solid). Shown in FIG. 20B, curve 2003 is the excitation spectrum for Texas Red (dotted line); curve 2004 is the corresponding emission spectrum (solid). Here control is Channel B (FIG. 20B) and target is Channel A (FIG. 20A), but the assignment is arbitrary.

Boxed area ExA indicates the wavelength band that is allowed to pass through the target excitation bandpass filter 1333 (cf FIG. 13). Box EmA indicates the wavelength band that is allowed to pass through the target emission bandpass filter 1335. Box ExB indicates the wavelength band that is allowed to pass through the control excitation bandpass filter 1313. Box EmB indicates the wavelength band that is allowed to pass through the control emission bandpass filter 1315. The boxes indicate the presence of stopbands on either side of the maxima. It can be seen from FIGS. 20A and 20B that, given the spectra for these two fluorophores and optical filters having the passband characteristics configured as shown, the following error conditions are corrected:

a. Long wavelength excitation light from the target LED 1331 (greater than the wavelength of the LED peak excitation) cannot be mistakenly confused for target fluorescent emission, due to these longer wavelengths being cut off by the LED excitation filter 1333.

b. Long wavelength excitation light from the control LED 1311 (greater than the wavelength of the LED peak excitation) cannot be mistakenly confused for control fluorescent emission, due to these longer wavelengths being cut off by the LED excitation filter 1313.

c. Target fluorescent emissions cannot be inadvertently triggered by the (excitation filtered) control LED 1311. This error condition would otherwise lead to the control photosensor 1317 receiving unwanted contemporaneous signals from both the target and control fluorophores.

d. Control fluorescent emissions cannot be inadvertently triggered by the (excitation filtered) target LED 1331. This error condition would otherwise lead to the target photosensor 1337 receiving unwanted contemporaneous signals from both the target and control fluorophores.

Figure 21A:
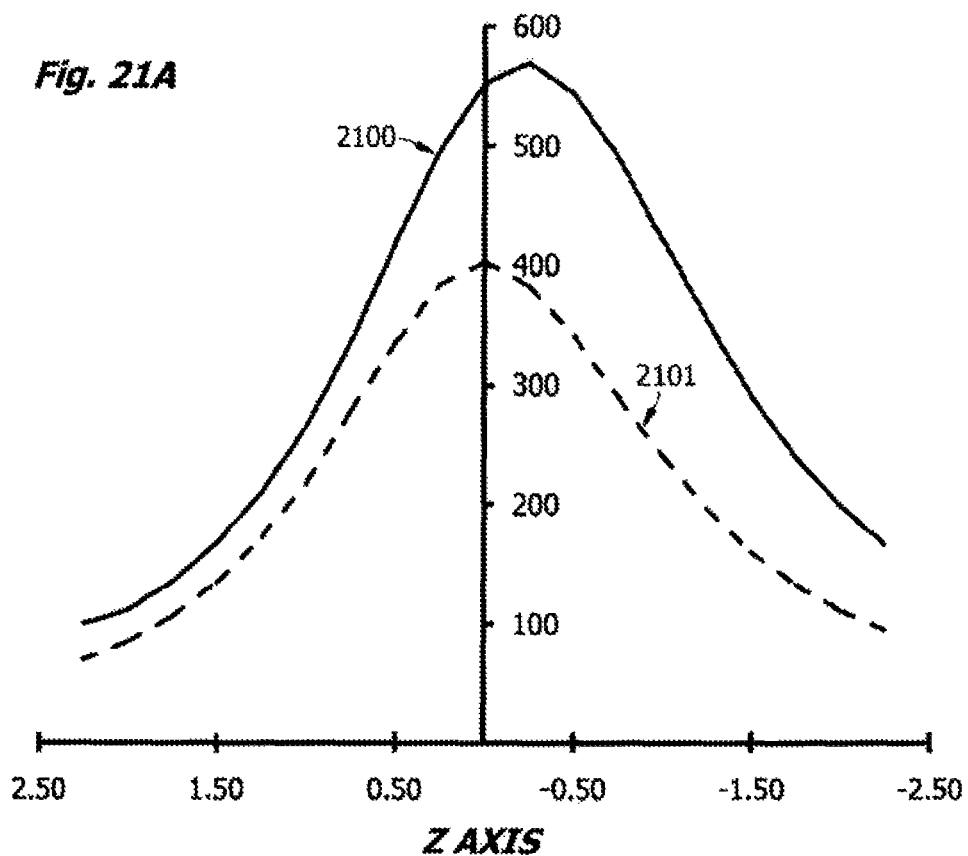
FIG. 21A plots experimental results demonstrating enhancement of signal output by varying the height of the objective lens above the mirror.

FIG. 21A plots experimental results demonstrating enhancement of fluorescent signal output by varying the height of the objective lens above the mirror. Briefly, fluorescent beads (Thermo Fisher Scientific, p/n G0300, Pittsburg, Pa.) were inserted into a microfluidic detection chamber and the detection chamber mounted under the objective lens 315 of the detector essentially as shown in FIG. 3A. Using a digital micrometer, the height of the detector head above the microfluidic cartridge was then varied to construct the plot. In a second paired experiment, the mirrored surface was removed. The solid line (2100) shows the effect of varying the lens height in the presence of a mirror on the heating block; the dotted line (2101) shows the effect of varying lens height in the absence of a back mirror. As can be seen, the presence of the mirror seems to shift the optimal emission maximum behind the mirror plane (i.e. a composite of the real and virtual fluorescent emissions captured in the lens).

Figure 21B:
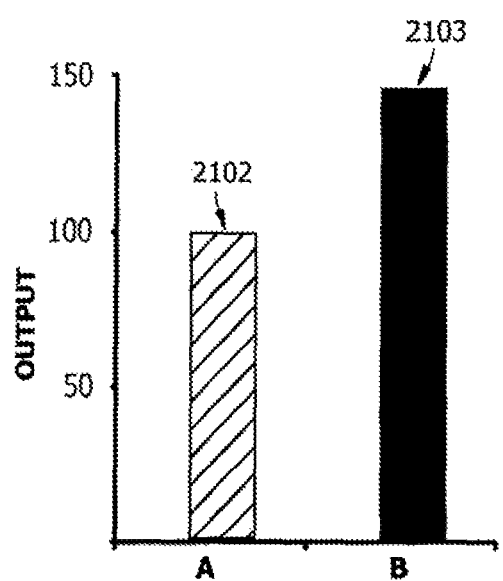
FIG. 21B graphs the integrated output signal strength with and without the back mirror. Output signal was found to be optimized by focusing the excitation beam at a focal point behind the mirror as shown in FIG. 15 and collecting emissions at a shorter working distance as shown in FIG. 16.

FIG. 21B graphs the integrated output signal strength with (2103) and without (2102) the back mirror. Output signal was found to be optimized by focusing the excitation beam at a focal point behind the mirror as shown in FIG. 15 and collecting emissions at a shorter working distance as shown in FIG. 16.

In a second experiment, the detection chamber is filled with a liquid sample containing a soluble fluorophore and pumped through the chamber at constant rate so as to avoid quenching artifact. The detector head height is then varied as before and the optimal detector height determined. In related experiments, the working distance of the sensor lens and objective lens are also varied so as to optimize sensitivity and limit of detection. We learn that optimal configuration is not achieved when the objective lens is centered in the detection chamber and the other lenses are made confocal. When a mirror is used, decoupled optics achieve advantageous results, a technological advance in the field.

Figure 22:
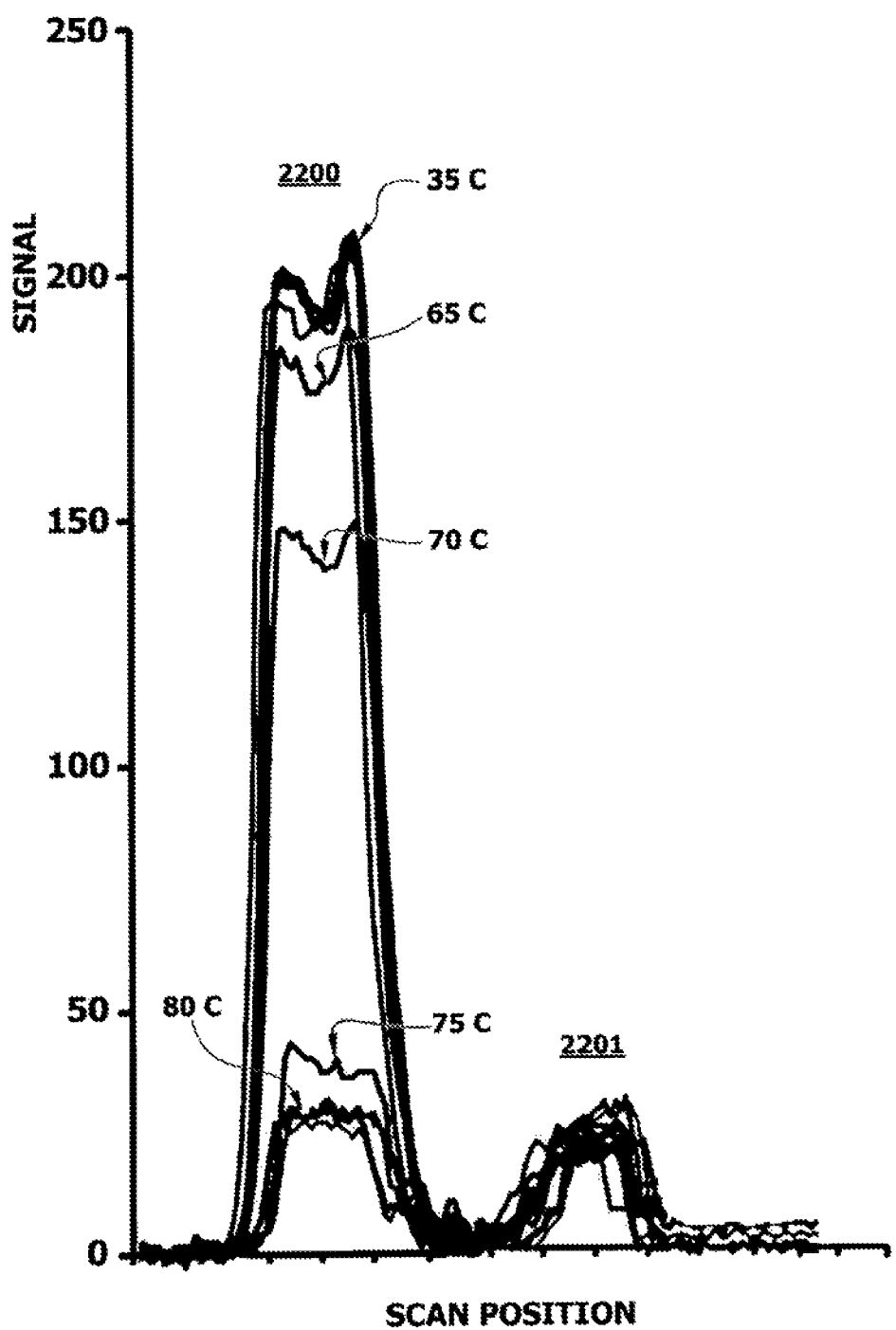
FIGS. 22 and 23A and 23B demonstrate a thermal melt curve of a molecular beacon hybridized to an amplicon.
Figure 23A:
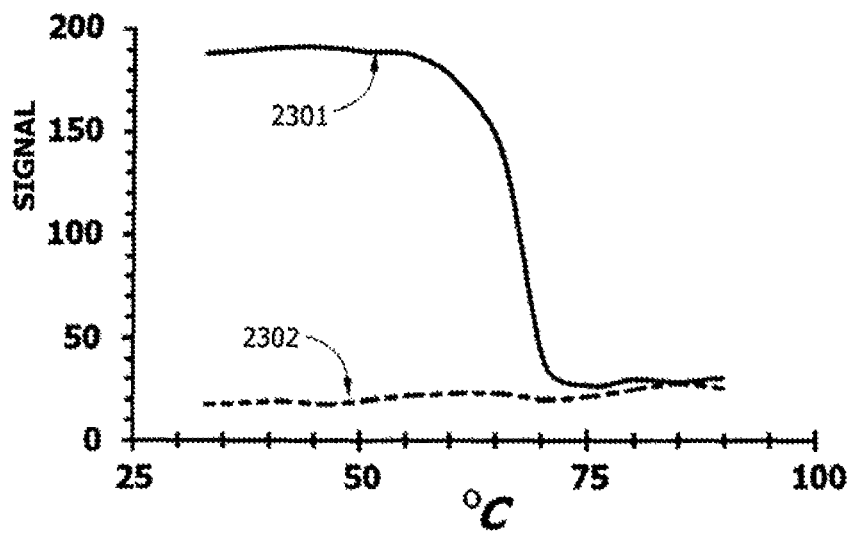
Figure 23B:
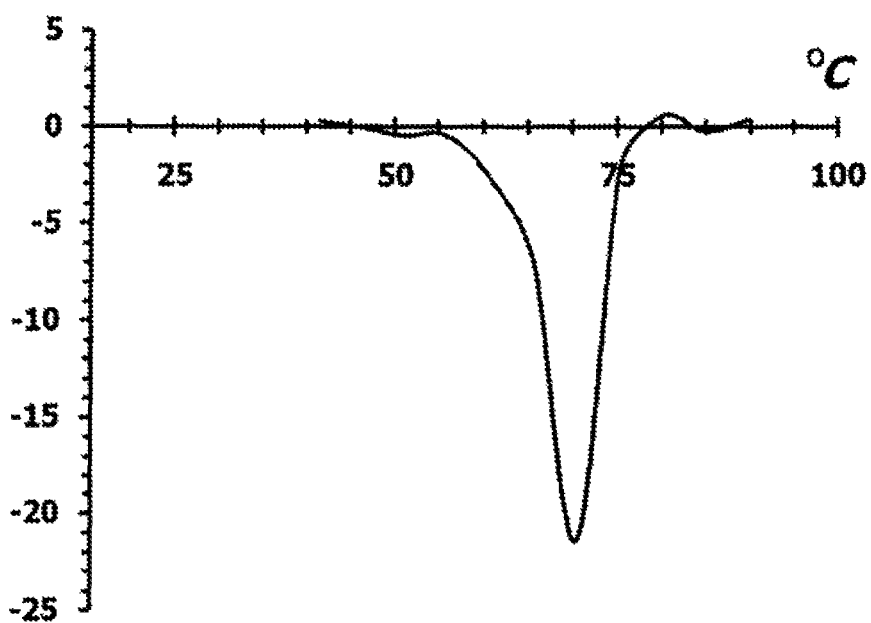

FIG. 22 shows scanning data collected for a molecular beacon hybridized to an amplicon. The scanning axis transects detection wells (2200,2201) representing positive and negative test conditions respectively, and it can be seen that signal is limited to the detection wells. In the figure, the sample is scanned repetitively as the temperature in the detection chamber is systematically varied. The scans are overlaid in the plot to illustrate the spatial resolution of the data. Fluorescence scans for 35° C., 65° C., 70° C., 75° C. and 80° C. test conditions are marked. Test plots at 40, 45, 50, 55, and 60° C., and the 85 and 90° C. plots were not well differentiated, as expected, and are not individually marked. It can be seen that fluorescent signal is a function of temperature. Fluorescence quenching is observed to increase as the double stranded probe-target is melted, ie. signal is greatest at 35° C. and is essentially not present at 80° C. In FIG. 23A, the data is plotted for signal versus temperature for the positive (2301, solid line) and negative (2302, dotted line) test conditions. In FIG. 23B, a first derivative is plotted, indicating a FRET melt temperature of about 70° C.

EXAMPLE I

In this example, the apparatus of the invention is shown to be useful in diagnosis of infectious disease by detection of the nucleic acids of a pathogen in a human sample such as blood. Using on-board dry and liquid reagents, a blood sample is processed and DNA associated with *Plasmodium falciparum* is detected in about 30 minutes or less. DNA purified from the sample is subjected to PCR using two microfluidic chambers with dual temperature zones as described in U.S. Pat. No. 7,544,506 and U.S. patent application Ser. No. 11/562,611 (Microfluidic Mixing and Analytical Apparatus), which are coassigned. Amplicon is then detected using a FAM fluorescence-tagged molecular beacon directed at the amplified target. Optionally, a control consisting of a California Red-tagged RNAaseP leukocyte exon sequence, with multiplex amplification, is used to validate the assay. A representative thermal melt curve obtained using the thermo-optical interface of the invention is shown in FIG. 22A.

EXAMPLE II

The apparatus of the invention is useful in the diagnosis of coagulopathies. Using on-board dry and liquid reagents, a blood sample is assayed for Coagulation Factor VIIa deficiency by incubating plasma with a fluorogenic substrate such as (D-Phe-Pro-Arg-ANSNH-cyclohexyl-2HCl; F.W.=777.81, Haematologic Technologies, Essex Junction, VT) where ANSN is fluorophore 6-amino-1-naphthalene-sulfonamide, which lights up when the amide bond between the dye and the peptide is cleaved. Tissue Factor (TF) is obtained from Calbiochem (LaJolla Calif.) and incorporated into phosphatidylcholine or phosphatidylserine vesicles before use. TF is used in excess. A 100 uL substrate reaction mixture consisting of 20 mM Hepes buffer, pH 7.4, 0.15 M NaCl, with 5 nM TF and containing 20 uM EDTA is incubated with a plasma sample for 10 min to form the active enzyme complex. The ANSH substrate is then added. The rate of hydrolysis of substrate is linear over the normal range of Factor VIIa, and can be determined from a standard curve. Descriptions of assay development may be found in US Patent Application 2009/0325203 and other experimental literature.

While the above is a description of the preferred embodiments of the present invention, it is possible to use various alternatives, modifications and equivalents. Therefore, the scope of the present invention should be determined not with reference to the above description but should, instead, be determined with reference to the appended claims, along with their full scope of equivalents. The appended claims are not to be interpreted as including means-plus-function limitations, unless such a limitation is explicitly recited in a given claim using the phrase "means for."

All of the U.S. patents, U.S. patent application publications, U.S. patent applications, foreign patents, foreign patent applications and non-patent publications referred to in this specification, are incorporated herein by reference, in their entirety. Aspects of the embodiments can be modified, if necessary to employ concepts of the various patents, applications and publications to provide yet further embodiments.

What is claimed is:

1. An apparatus comprising a scanning detector head having two or more optical channels for detecting at least one fluorescence signal in a liquid sample, the apparatus comprising a chassis having a docking port for receiving a disposable microfluidic cartridge therein, the microfluidic cartridge comprising a detection chamber, the detection chamber having a first optical window and a second optical window oppositely disposed thereon; wherein,
   a) the second optical window is a thermo-optical window formed of a compliant thermo-optical film;
   b) the scanning detector head comprises a drive train configured to guidedly scan across the detection chamber, the chassis further having a clamping mechanism for clamping the microfluidic cartridge in the docking port and for urging the compliant thermo-optical film of the microfluidic cartridge into thermoconductive contact with a heating element affixed to the chassis;
   c) each optical channel comprises an objective lens, a light source with source lens for transitioning excitation light through the objective lens and into the detection chamber, a dichroic beamsplitter and an emission detection sensor with emission sensor lens; and
   d) the heating element is surfaced with a mirror face positioned to thermo-optically contact the second optical window; and the heating element with mirror face is configured for reflecting excitation and emission light incident thereon back into the objective lens, while also controlling or adjusting the temperature in the detection chamber; and
   wherein for each of the optical channels, the light source is positioned at a first distance from the source tens, the native focal point of the source lens is at second distance from the source lens, wherein the first distance is not the same as the second distance, such that the focal point of the excitation light through the objective lens is at a third distance from the objective lens, the native focal point of the objective lens is at a fourth distance from the objective lens and third distance is not equal to the fourth distance.

2. The apparatus of claim 1, wherein the first distance is less than the second distance.

3. The apparatus of claim 1, wherein the source lens is configured to form a diverging excitation beam of light incident on the objective lens.

4. The apparatus of claim 1, wherein the compliant thermo-optical film is a flexible plastic film having low resistance to heat transfer and optical transparency over a spectrum of excitation and emission wavelengths.

5. The apparatus of claim 1, wherein the apparatus comprises a programmable host controller, the scanning detector head comprises an embedded microprocessor, and the optical channels each comprise an amplifier configured for amplifying a voltage from the detection sensor; and wherein the embedded microprocessor is operatively coupled with a clock and firmware for processing the amplified voltages and for outputting digital signals indicative of a result of a fluorescence assay to the programmable host controller.

6. The apparatus of claim 5, wherein the embedded microprocessor is configured for strobing a source LED at a strobe rate and with a selectable pulse width configured to effectively filter electrical or ambient noise.

7. The apparatus of claim 5, wherein the embedded microprocessor is configured to sum all positive digital signals for any amplified voltages greater than a threshold value and all neutral digital signals for any amplified voltage less than a threshold value, and output the sum to the programmable host controller while scanning the detection chamber, and the programmable host controller is configured to report a qualitative result for the fluorescence assay, such that the assay result is independent of bubble interference.

8. The apparatus of claim 5, wherein the programmable host controller is configured for digitally receiving the digital signals and displaying or electronically outputting the result of the fluorescence assay.

9. The apparatus of claim 8, wherein the fluorescence assay is an assay for a nucleic acid target in a biological sample, and the microfluidic cartridge is configured for amplifying the nucleic acid target to form an amplicon.

10. The apparatus of claim 9, wherein the microfluidic cartridge comprises a dehydrated primer tagged with a fluorophore.

11. The apparatus of claim 10, wherein the primer is a scorpion primer, an amplifluor primer, a black hole primer, a Qzyme primer or a LUX primer.

12. The apparatus of claim 9, wherein the amplicon is detected by a fluorescence detection with a molecular beacon probe, a FRET probe, a TaqMan Probe, a dual oligo FRET-based probe (Roche), a minor groove binder-conjugated hybridization probe, an Eclipse probe, a locked nucleic acid probe or an intercalation probe.

13. The apparatus of claim 9, wherein amplifying the nucleic acid target comprises a PCR thermocycling step.

14. The apparatus of claim 8, wherein the assay is a fluorescence assay for a protein target analyte in the liquid sample.

15. The apparatus of claim 1, wherein the third distance is greater than the fourth distance.

16. The apparatus of claim 1, wherein the focal point of the emission light through the objective lens is at or behind the mirror face.

17. The apparatus of claim 16, wherein the native focal point of the objective lens is between the first and second optical windows.

18. The apparatus of claim 1, wherein the focal point of emission light through the emission sensor lens is at a fifth distance from the emission sensor lens, and the fourth distance is equal to the fifth distance.

* * * * *

UNITED STATES PATENT AND TRADEMARK OFFICE
CERTIFICATE OF CORRECTION

PATENT NO. : 8,431,389 B2  
APPLICATION NO. : 13/245124  
DATED : April 30, 2013  
INVENTOR(S) : C. Frederick Battrell et al.

It is certified that error appears in the above-identified patent and that said Letters Patent is hereby corrected as shown below:

In the Claims

Column 30, Line 29, Claim 1:
"positioned at a first distance from the source tens, the" should read, --positioned at a first distance from the source lens, the--.

Signed and Sealed this
Seventh Day of January, 2014

Margaret A. Focarino
*Commissioner for Patents of the United States Patent and Trademark Office*